US011203766B2

(12) United States Patent
Kock et al.

(10) Patent No.: US 11,203,766 B2
(45) Date of Patent: *Dec. 21, 2021

(54) *PERONOSPORA* RESISTANCE IN *SPINACIA OLERACEA*

(71) Applicant: RUK ZWAAN ZAADTEELT EN ZAADHANDEL B.V., De Lier (NL)

(72) Inventors: Vincent Laurens Adrianus Kock, De Lier (NL); Raoul Jacobus Johannes Maria Frijters, De Lier (NL); Johannes Geert Jan Feitsma, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/361,491

(22) Filed: Mar. 22, 2019

(65) Prior Publication Data

US 2019/0233841 A1   Aug. 1, 2019

Related U.S. Application Data

(63) Continuation-in-part of application No. PCT/EP2017/074807, filed on Sep. 29, 2017.

(30) Foreign Application Priority Data

Sep. 30, 2016  (WO) ............... PCT/EP2016/001624

(51) Int. Cl.
| | |
|---|---|
| *C12N 15/82* | (2006.01) |
| *A01H 5/12* | (2018.01) |
| *A01H 6/02* | (2018.01) |
| *C12Q 1/6895* | (2018.01) |

(52) U.S. Cl.
CPC ........... *C12N 15/8282* (2013.01); *A01H 5/12* (2013.01); *A01H 6/028* (2018.05); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 9,265,275 | B2 | 2/2016 | Den Braber |
| 9,402,363 | B1* | 8/2016 | Feitsma et al. .......... A01H 5/12 |
| 10,017,781 | B2 | 7/2018 | Torjek et al. |
| 10,633,670 | B2* | 4/2020 | Kock et al. ........ C12N 15/8282 |
| 2005/0183150 | A1 | 8/2005 | Torisky et al. |
| 2007/0204368 | A1 | 8/2007 | Dale |
| 2009/0300786 | A1 | 12/2009 | Baerends |
| 2009/0300788 | A1 | 12/2009 | Baerends |
| 2010/0031385 | A1 | 2/2010 | Baerends |
| 2012/0054894 | A1 | 3/2012 | Den Braber |
| 2013/0055422 | A1 | 2/2013 | Baerends |
| 2013/0055454 | A1 | 2/2013 | Den Braber |
| 2013/0230635 | A1* | 9/2013 | den Braber ........ C12N 15/8282 426/615 |
| 2014/0065287 | A1 | 3/2014 | Den Braber |
| 2014/0068799 | A1 | 3/2014 | Den Braber |
| 2014/0068801 | A1 | 3/2014 | Den Braber |
| 2014/0068804 | A1 | 3/2014 | Den Braber |
| 2014/0068805 | A1 | 3/2014 | Den Braber |
| 2014/0068806 | A1 | 3/2014 | Den Braber |
| 2015/0082483 | A1* | 3/2015 | Dijkstra ................... A01H 5/12 800/279 |
| 2015/0101073 | A1 | 4/2015 | Brugmans et al. |
| 2015/0240256 | A1 | 8/2015 | Brugmans et al. |
| 2016/0152999 | A1 | 6/2016 | Torjek et al. |
| 2016/0177330 | A1* | 6/2016 | Dijkstra ............. C12N 15/8282 800/265 |
| 2017/0027126 | A1 | 2/2017 | Dijkstra et al. |
| 2017/0027127 | A1 | 2/2017 | Dijkstra et al. |
| 2017/0327839 | A1* | 11/2017 | Feitsma ................... A01H 5/12 |

(Continued)

FOREIGN PATENT DOCUMENTS

| | | |
|---|---|---|
| DE | 10 2013 010026 A1 | 12/2014 |
| EP | 2 848 114 A1 | 3/2015 |
| EP | 2 912 940 A1 | 9/2015 |

(Continued)

OTHER PUBLICATIONS

NCBI Blast (2020) Seq ID No. 6 v. Patent database.*
NCBI Blast (2020) Seq ID No. 7 v. Patent database.*
Correll et al. (2011) Eur J Plant Pathol 129:193-205.*
Qi & Innes (2013) Front Immunol 4:348.*
Irish et al. (2007) Plant Dis 91:1392-96.*
Bentham et al. (2017) Annals Bot 119:689-702.*
Sukarta et al. (2016) Sem Cell Devol Biol 56:134-49.*
Dodds et al. (2001) Plant Cell 13:163-78.*
Chakraborty et al. (2018) Plant Sci 269:85-93.*
Eitas & Dangl (2010) Curr Opin Plant Biol 13:472-77.*
She et al. (2018) Theor Appl Genet 131:2529-41.*
2011 APS-IPPC Joint Meeting Abstracts of Presentations, Phytopathology (2011) 101(6) Supplemental, S1, S52.

(Continued)

*Primary Examiner* — Russell T Boggs
(74) *Attorney, Agent, or Firm* — Duane Morris LLP; Thomas J. Kowalski; Deborah L. Lu

(57) ABSTRACT

The present invention relates to an allele designated alpha-WOLF 15 which confers resistance to at least one *Peronospora farinosa* f. Sp. *spinacea* race, wherein the protein encoded by said allele is a CC-NBS-LRR protein that comprises in its amino acid sequence: a) the motif "MAEIGYSVC" (SEQ ID NO: 13) at its N-terminus; and b) the motif "KWMCLR" (SEQ ID NO: 14); and wherein the LRR domain of the protein has in order of increased preference at least 92%, 93%, 94%, 95%, 96%, 97%, 98%, 99%, 100% sequence similarity to SEQ ID NO: 10. The allele when homozygously present in a spinach plant confers complete resistance to *Peronospora farinosa* f. Sp. *spinacea* races pfs:1, pfs:2, pfs:3, pfs:4 and pfs:5, pfs:6, pfs:8, pfs:9, pfs:11, pfs:12, pfs:13, pfs:14, pfs:15, pfs:16 and isolates UA1014 and US1508, and confers intermediate resistance to pfs:10, and does not confer resistance to pfs:7.

3 Claims, No Drawings
Specification includes a Sequence Listing.

(56) References Cited

U.S. PATENT DOCUMENTS

| | | |
|---|---|---|
| 2018/0042198 A1 | 2/2018 | Feitsma |
| 2019/0127753 A1* | 5/2019 | Kock et al. ........ C12N 15/8282 426/615 |

FOREIGN PATENT DOCUMENTS

| | | |
|---|---|---|
| WO | 2013/064436 A1 | 5/2013 |
| WO | 2015/036378 A1 | 3/2015 |
| WO | 2015/036469 A1 | 3/2015 |
| WO | 2018/059653 A1 | 4/2018 |

OTHER PUBLICATIONS

Adam Bentham, et al., Animal NLRs Provide Structural Insights into Plant NLF Function, Annals of Botany (2017) 119:689-702.

Joydeep Chakraborty, et al., Functional Diversification of Structurally Alike NLR Proteins in Plants, Plant Science (2018) 269:85-93.

Peter N. Dodds, et al., Six Amino Acid Changes Confined to the Leucine-Rich Repeat β-Strand/β-Turn Motif Determine the Difference between the P and P2 Rust Resistance Specificities in Flax, The Plant Cell (Jan. 2001) vol. 13, p. 163-178.

Timothy K. Eitas, et al., NB-LRR Proteins: Pairs, Pieces, Perception, Partners, and Pathways, Current Opinion in Plant Biology (2010) 13:472-477.

Feng, et al., Identification of New Races and Deviating Strains of the Spinach Downy Mildew Pathogen *Peronospora farinosa* f. sp. *spinaciae*. Plant Disease (Jan. 2014) 98(1):145-152.

GenBank Accession No. XP_021642255 (Aug. 1, 2017).

Haiwei H. Guo, et al., Protein Tolerance to Random Amino Acid Change, PNAS (Jun. 22, 2004) vol. 101, No. 25, p. 9205-9210.

Charlotte Hallavant, et al., The First Archaeobotanical Evidence of *Spinacia oleracea* L. (Spinach) in Late 12th-mid 13th Century A.D. France, French National Centre for Scientific Research, Article: Vegetation History and Archaeobotany, Published online May 21, 2013.

B. M. Irish, et al., Three New Races of the Spinach Downy Mildew Pathogen Identified by a Modified Set of Spinach Differentials, Plant Disease (Nov. 2007) vol. 91, No. 11, p. 1392-1396.

Merriam Webster Definition of "as" Sep. 27, 2016.

Simona Proietti, et al., Increase of Ascorbic Acid Content and Nutritional Quality in Spinach Leaves During Physiological Acclimation to Low Temperature, Plant Physiology and Biochemistry (2009) vol. 47, p. 717-723.

Dong Qi, et al., Recent Advances in Plant NLR Structure, Function, Localization, and Signaling, Frontiers in Immunology (2013) vol. 4, Article 348, p. 1-10.

Hongbing She, et al., Fine Mapping and Candidate Gene Screening of the Downy Mildew Resistance Gene RPF1 in Spinach, Theoretical and Applied Genetics (2018) 131:2529-2541.

Octavina C.A. Sukarta, et al., Structure-Informed Insights for NLR Functioning in Plant Immunity, Seminars in Cell & Developmental Biology (2016) 56:134-148.

Yanming Yang, et al., Transgenic Spinach Plants Expressing the Coat Protein of Cucumber Mosaic Virus, In Vitro Cell Dev. Biol.-Plant (1997) 33:200-204.

Feng Chunda, et al., Construction of a Spinach Bacterial Artificial Chromosome (BAC) Library as a Resource for Gene Identification and Marker Development, Plant Mol Biol Rep (2015) 33:1996-2005.

B. M. Irish, et al., Characterization of a Resistance Locus (Pfs-1) to the Spinach Downy Mildew Pathogen *(Peronospora farinosa* f. sp. *spinaciae)* and Development of a Molecular Marker Linked to Pfs-1, Pathology, American Phytopathological Society, US (2008) vol. 98, No. 8, p. 894-900.

J.C. Correll, et al., Spinach: Better Management of Downy Mildew and White Rust Through Genomics, Eur. J. Plant Pathology (Dec. 4, 2010) 129:193-205.

International Search Report and Written Opinion dated Dec. 14, 2017 in PCT/EP2017/074807.

* cited by examiner

SEQUENCE LISTING

```
<160> NUMBER OF SEQ ID NOS: 18

<210> SEQ ID NO 1
<211> LENGTH: 6853
<212> TYPE: DNA
<213> ORGANISM: Spinacia oleracea
```

<400> SEQUENCE: 1

```
atggccgaaa tcggatactc ggtttgtgcg aaactcatcg aagtgattgg cagtgagctg      60
atcaaagaga tttgtgacac atggggttac aaatctcttc ttgaggacct caacaaaact     120
gtattgacgg tcaggaacgt tctcattcaa gccggggtga tgcggagct tactagtgaa     180
caacaaggtt tcattgcaga ccttaaagat gttgtttatg atgctgatga cttgttcgac     240
aagttactca ctcgtgctga gcgaaaacag attgatggaa acgaaatctc tgaaaaggta     300
cgtcgtttct tttcctctag taacaagatc ggtcaagctt actacatgtc tcgtaaggtt     360
aaggaaatta agaagcagtt ggatgaaatt gttgataggc atacaaaatt tgggtttagt     420
gccgagttta tacctgtttg tagggaaagg gggaacgaga gggaaacacg ttcatatata     480
gatgtcaaga atattcttgg gagggataaa gataagaatg atatcataga taggttgctt     540
aatcgtaatg gtaatgaagc ttgtagtttc ctgaccatag tgggagcggg aggattggga     600
aaaactgctc ttgcacaact tgtgttcaat gatgaaaggg tcaaaattga gttccatgat     660
ttgaggtatt gggtttgtgt ctctgatcaa gatgggggcc aatttgatgt gaaagaaatc     720
ctttgtaaga ttttagaggt ggttactaag agaaagttg ataatagttc cacattggaa     780
ttggtacaaa gccaatttca agagaagtta agaggaaaga agtacttcct tgttcttgat     840
gatgtatgga cgaagatcg tgagaagtgg cttcctttgg aagagttgtt aatgttgggt     900
caaggggaa gcaaggttgt agtgaccgca cgttcagaga agacagcaaa tgtcataggg     960
aaaagacatt tttatacact ggaatgtttg tcaccagatt attcatggag cttatttgaa    1020
atgtcggctt ttcagaaagg gcatgagcag gaaaaccatc acgaactagt tgatattggg    1080
aaaagattg ttgaaaaatg ttataacaat ccacttgcta taacggtggt aggaagtctt    1140
ctttatggag aggagataag taagtggcgg tcatttgaaa tgagtgagtt ggccaaaatt    1200
ggcaatgggg ataataagat tttgccgata ttaaagctca gttaccataa tcttataccc    1260
tcgttgaaga gttgcttcag ttattgtgca gtgtttccca aggatcatga ataaagaag    1320
gagatgttga ttgatctttg gatagcacaa ggatacgttg tggcacttga tggaggtcaa    1380
agtatagaag atgctgccga agaacatttt gtaattttgt tacggagatg tttctttcaa    1440
gatgtaaaga aggatgaata tggtgatgtt gattctgtta aaatccacga cttgatgcac    1500
gatgtcgccc aagaagtggg gagggaggaa atatgtgtag tgaatgataa tacaaagaac    1560
ttgggtgata aaatccgtca tgtacatggt gatgtcaata gatatgcaca aagagtctct    1620
ctgtgtagcc atagccataa gattcgttcg tatattggtg gtgattgtga aaacgttgt    1680
gtggatacac taatagacaa gtggatgtgt cttaggatgt tggacttgtc atggtcggat    1740
gttaaaaatt tgcctaattc aataggtaaa ttgttgcact tgaggtatct taacctgtca    1800
gataatagaa atctaaagat acttcctgat gcaattacaa gactgcataa tttgcagaca    1860
ctgcttttag aagattgcag aagtttaaag gagttgccaa agattttttg caaattggtc    1920
aaactgaggc acttggaatt acagggttgt catgatttga ttggtatgcc atttggaatg    1980
gataagctaa ctagtcttag aatactacca aacattgtgg tgggtaggaa ggaacaaagt    2040
gatgatgagc tgaaagccct aaaaggcctc accgagataa aaggctccat ttctatcaga    2100
atctattcaa agtatagaat agttgaaggc atgaatgaca caggaggagc tgcttatttg    2160
aagagcatga acatctcag ggagattgat attcattttt gggtgaatg tgttggccct    2220
gaagctgtat tggaaacctt agagccacct tcaaatatca agagcttata tatatataat    2280
```

```
tacagtggta caacaattcc agtatgggga agagcagaga ttaattgggc aatctccctc    2340
tcacatctcg tcgacatcca gcttagttgt tgtagtaatt tgcaggagat gccagtgctg    2400
agtaaactgc ctcatttgaa atcgctgaaa cttggatggt tggataactt agagtacatg    2460
gagagtagca gtagcagtga cacagaagca gcaacaccag aattaccaac attcttccct    2520
tcccttgaaa aacttacttt acagcatctg gaaaagttga agggttttgg gaacaggaga    2580
tcgagtagtt ttccccgcct ctctgaattg gaaatcaaga aatgcccaga tctaacgtca    2640
tttccttctt gtccaagcct tgagaagttg gaattgaaag aaagcaatga agcattgcaa    2700
ataatagtaa aaataacaac aagaggtaaa gaaaaagaag agaacaataa tgctggtgtt    2760
agaaattcac aagatgatga caaagtcaaa ttacggaaga tggtgataga caatctgggt    2820
tatctcacgg gggttgatat tagatttgat gatagagaag gtggatttgt taaccctgaa    2880
gctgtgttgg caaccctaga gccaccttca aatatcaaga gcttatctat acatcgtttt    2940
gatggtaaaa cacttccagt atggggaaga gcagagatta attgggcaat ctccctctca    3000
catcttgtcg acatccagct ttggcattgt cgtaatttgc aggagatgcc agtgctgagt    3060
aaactgcctc atttgaaatc actggaactt tataatttga ttagtttaga gtacatggag    3120
agcacaagca aagcagtag cagtgacaca gaagcagcaa caccagaatt accaacattc    3180
ttcccttccc ttgaaaaact tagactttgg tatctggaaa agttgaaggg tttggggaac    3240
aggagaccga gtagttttcc ccgcctctct gaattggaaa tctgggaatg cccagatcta    3300
acgtggtttc ctccttgtcc aagccttaaa acgttgaaat tggaaaaaaa caatgaagcg    3360
ttgcaaataa tagtaaaaat aacaacaaca agaggtaaag aagaaaaaga agaagacaag    3420
aatgctggtg ttggaaattc acaagatgat gacaatgtca aattacggaa ggtggaaata    3480
gacaatgtga gttatctcaa atcactgccc acaaattgtc ttactcacct caaaataact    3540
ggaatagatt acagggaggg ggagattgaa tcagattccg tggaggagga gattgaattg    3600
gaagttgggg aggcatttca gaagtgtgca tcttcttga gaagcctcat cataatcgga    3660
aatcacggaa taaataaagt gatgagactg tctggaagaa cagggttgga gcatttcact    3720
ctgttggact cactcaaatt ttcaaagata gaagaccagg aagatgaggg cgaagacaac    3780
atcatattct ggaaatcctt tcctcaaaac cttcgcagtt tgagaattaa agactctgac    3840
aaaatgacaa gtttgcccat ggggatgcag tacttaacct ccctccaaac cctcgaacta    3900
tcatattgtg atgaattgaa ttcccttcca gaatggataa gcagcttatc atctcttcaa    3960
tacctgcgca tatactactg tccagccctg aaatcactac cagaagcaat gcggaacctc    4020
acctcccttc agacacttgg gatatcggat tgtccagacc tagttaaaag atgcagaaaa    4080
cccaacggca aggactatcc caaaattcaa cacatcccca aaattgtaag tcattgcaga    4140
aagtaattta ttcatttata tttattttat gcttagaatg atatacgcag tcgtcctttg    4200
gtttcaaatc ttgaatttgg ttttttgtttt cttttctttgt ttcttattc aacaccagcc    4260
catttatgat tgattcatta aaaaaaggat ggagttttat ggatttgaag aagacaacga    4320
attgagattc ctgggggtttt cttttttgttg gggttggatt tcatgtatat gttgctgatt    4380
aaatacgaga ctgatgatga tgatgtgttt atgggttta aatcagatta aatatatggg    4440
aaatgcaagt taatttggga tgcacataag gtgtttgctg aaatgtctat gagaaatgtt    4500
gtttcttgga cttagaatga tatacactgt cgtcctttgg tttccaatct tacatttggt    4560
ttgtgttttc ttagtttgtt tctttaatca acaccaaccc gttttttta aactacctgc    4620
aactactaat ttacgtttac cctgtatctc aggtactaaa tgaatattgg tgattttcag    4680
```

```
ttactcaaca ctagcttgat cctgaacgca cccaaccttc aggttagaat ccggcttact    4740
catccttttg tccagttttc aagtaattgt tttggcagga tcaattctct aattgttgta    4800
caccgtatat tgcaatttat agtgactaca gttaatgaat gtttacaaaa aattagtcat    4860
gtaaaaactt cttctctgtc cattacataa actcttttc tctttctaac ttatcatgtt     4920
catgtctaaa caattaaaca tgctcacatc aatgttcatt taagctaact tacttctgta    4980
agagagcgag ctagttaaaa actcctttaa ctttctgttt tatactcagg acatggattg    5040
atgcaagcat gaagaacttc gggaatttgc taaaactcta ccaaagcgat gagagtttgg    5100
actttatttc acttgaagtc agggactgtc aacaaagcca cagtgtgcat gttggctgtt    5160
tcacttggac gataaaaagg tttatttaat tgttttccta agtgtatttg cttacaagc     5220 ttttactttt cacttgaaag ggttttttctt gttttaagct tttcgaatta gagttttcgg    5280
ttgaagtaag agtagtcgta ttagtctttt acctaaggaa gactcttttt tgtaattttc    5340
agactatgca attcaagttt tcgagtgttt tcttgcttgt gtgattgtga gttggtgaat    5400
tcgtctttca tacattttga gattatcaga agctttatgc tccaccggta gtctagtacc    5460
ttttctgtta ctgtgcaggg aagtaatctg gtaccttcta tatatgtgga aaaacataca    5520
ttatacatta tgcaaaattc ttacaggtta gttacttcct ggaacttcat ttacacttag    5580
ttttttttgt tccattccct cggaatcaag tcattccctc tgagaaatat gtaatgaact    5640
tctgtatgtt gctgtttggt tcctgttta atcttcaatt ttcttgtata gttacagctg     5700
catttacaat gaagtttaag cagacactct ctttatatag tgcctctttc tggagcaccg    5760
tagagctgtc tgtggttgat caccatctgc tgccgagaga ttcagcaatc gcgtgtttga    5820
tcaggtaaaa gttttttatgt caatgtgttt tttttttccgt ttgatcaatt tatgtctgta    5880
ttcagattct tatcttctta cagtagcata acacattgtt tctttcattt atgtaaactg    5940
tttcaagatt acagagatgt atgcttcagt cgacattgat gataacttaa gatggcattc    6000
ctacaacagt tgcaggcgca ttctaactcc ggcaattcta gttaggcaag aggagcattg    6060
ccaatacctg ccacctctgg gatttactat accagggttg aagtttatgg aagacaccag    6120
ctatgcacaa gccttcaagg ggtcatccta cataacaagt tgaaccaacc aattgcttgt    6180
tggttcagtg gtaattgaag ctgaatttgg tagggatggc ccgtgttcga tccccacaac    6240
aacaattggg aggggactgg aacctatcca cacagaactc gccctgaatc cggattagcc    6300
ctaagggtga acggggtgct aacaccaaaa aaaaaaacat aacaagttga accaaacata    6360
ctttgtttga attgaagatt tagtgatttc atttgatcga ttgagatgtc ttattataag    6420
cgtatatgct cttggatttg gccacttagg tgttgtttga caattggaca ttaactcgct    6480
tttatatttt cttttctctt aggaaaggtg atcctgagaa tttatattgg aacactttt     6540 ttttctcact agctttaaaa aagtgttctg tgttacctgc aattcaattt gattattttt    6600
cacatagttt tacctgaaaa agtgttacct gaaaagtgt tacctgaaaa tcaactgaca     6660 taagttttg tttggatcca attaaggaca ctagataaat cggaataaat aatcaaccaa      6720
ttaagtactt cataattaaa tatgaagtgt attattatct tatgcttgtg acattgaagg    6780
atgttatgat attttaactc aataccttgc aaaatatact ggttaaattt cttaacaagg    6840
taacttggca aca                                                        6853
```

<210> SEQ ID NO 2
<211> LENGTH: 4146
<212> TYPE: DNA

<213> ORGANISM: Spinacia oleracea

<400> SEQUENCE: 2

```
atggccgaaa tcggatactc ggtttgtgcg aaactcatcg aagtgattgg cagtgagctg      60
atcaaagaga tttgtgacac atggggttac aaatctcttc ttgaggacct caacaaaact     120
gtattgacgg tcaggaacgt tctcattcaa gccggggtga tgcgggagct tactagtgaa     180
caacaaggtt tcattgcaga ccttaaagat gttgtttatg atgctgatga cttgttcgac     240
aagttactca ctcgtgctga gcgaaaacag attgatggaa acgaaatctc tgaaaaggta     300
cgtcgtttct tttcctctag taacaagatc ggtcaagctt actacatgtc tcgtaaggtt     360
aaggaaatta agaagcagtt ggatgaaatt gttgataggc atacaaaatt tgggtttagt     420
gccgagttta tacctgtttg tagggaaagg gggaacgaga gggaaacacg ttcatatata     480
gatgtcaaga atattcttgg gagggataaa gataagaatg atatcataga taggttgctt     540
aatcgtaatg gtaatgaagc ttgtagtttc ctgaccatag tgggagcggg aggattggga     600
aaaactgctc ttgcacaact tgtgttcaat gatgaaaggg tcaaaattga gttccatgat     660
ttgaggtatt gggtttgtgt ctctgatcaa gatgggggcc aatttgatgt gaaagaaatc     720
ctttgtaaga ttttagaggt ggttactaag agaaagttg ataatagttc cacattggaa     780
ttggtacaaa gccaatttca agagaagtta agaggaaaga agtacttcct tgttcttgat     840
gatgtatgga cgaagatcg tgagaagtgg cttcctttgg aagagttgtt aatgttgggt     900
caagggggaa gcaaggttgt agtgaccgca cgttcagaga agacagcaaa tgtcataggg     960
aaaagacatt tttatacact ggaatgtttg tcaccagatt attcatggag cttatttgaa    1020
atgtcggctt tcagaaagg gcatgagcag gaaaaccatc acgaactagt tgatattggg    1080
aaaaagattg ttgaaaaatg ttataacaat ccacttgcta taacggtggt aggaagtctt    1140
ctttatggag aggagataag taagtggcgg tcatttgaaa tgagtgagtt ggccaaaatt    1200
ggcaatgggg ataataagat tttgccgata ttaaagctca gttaccataa tcttataccc    1260
tcgttgaaga gttgcttcag ttattgtgca gtgtttccca aggatcatga aataaagaag    1320
gagatgttga ttgatctttg atagcacaa ggatacgttg tggcacttga tggaggtcaa    1380
agtatagaag atgctgccga gaacattttt gtaattttgt tacggagatg tttctttcaa    1440
gatgtaaaga aggatgaata tggtgatgtt gattctgtta aaatccacga cttgatgcac    1500
gatgtcgccc aagaagtggg gagggaggaa atatgtgtag tgaatgataa tacaaagaac    1560
ttgggtgata aaatccgtca tgtacatggt gatgtcaata gatatgcaca agagtctct    1620
ctgtgtagcc atagccataa gattcgttcg tatattggtg gtgattgtga aaaacgttgt    1680
gtggatacac taatagacaa gtggatgtgt cttaggatgt tggacttgtc atggtcggat    1740
gttaaaaatt tgcctaattc aataggtaaa ttgttgcact tgaggtatct taacctgtca    1800
gataatagaa atctaaagat acttcctgat gcaattacaa gactgcataa tttgcagaca    1860
ctgcttttag aagattgcag aagtttaaag gagttgccaa agattttttg caaattggtc    1920
aaactgaggc acttggaatt acagggttgt catgatttga ttggtatgcc atttggaatg    1980
gataagctaa ctagtcttag aatactacca acattgtgg tgggtaggaa ggaacaaagt    2040
gatgatgagc tgaaagccct aaaaggcctc accgagataa aaggctccat ttctatcaga    2100
atctattcaa gtatagaat agttgaaggc atgaatgaca caggaggagc tgcttatttg    2160
aagagcatga acatctcag ggagattgat attacatttt tgggtgaatg tgttggccct    2220
gaagctgtat tggaaaccct tagagccacct tcaaatatca agagcttata tatatataat    2280
```

| | |
|---|---:|
| tacagtggta caacaattcc agtatgggga agagcagaga ttaattgggc aatctccctc | 2340 |
| tcacatctcg tcgacatcca gcttagttgt tgtagtaatt tgcaggagat gccagtgctg | 2400 |
| agtaaactgc ctcatttgaa atcgctgaaa cttggatggt tggataactt agagtacatg | 2460 |
| gagagtagca gtagcagtga cacagaagca gcaacaccag aattaccaac attcttccct | 2520 |
| tcccttgaaa aacttacttt acagcatctg gaaaagttga agggttttgg gaacaggaga | 2580 |
| tcgagtagtt ttccccgcct ctctgaattg gaaatcaaga aatgcccaga tctaacgtca | 2640 |
| tttccttctt gtccaagcct tgagaagttg gaattgaaag aaagcaatga agcattgcaa | 2700 |
| ataatagtaa aaataacaac aagaggtaaa gaaaagaag agaacaataa tgctggtgtt | 2760 |
| agaaattcac aagatgatga caaagtcaaa ttacggaaga tggtgataga caatctgggt | 2820 |
| tatctcacgg gggttgatat tagatttgat gatagagaag gtggatttgt taaccctgaa | 2880 |
| gctgtgttgg caaccctaga gccaccttca aatatcaaga gcttatctat acatcgtttt | 2940 |
| gatggtaaaa cacttccagt atggggaaga gcagagatta ttgggcaat ctccctctca | 3000 |
| catcttgtcg acatccagct ttggcattgt cgtaatttgc aggagatgcc agtgctgagt | 3060 |
| aaactgcctc atttgaaatc actgaactt tataatttga ttagtttaga gtacatggag | 3120 |
| agcacaagca gaagcagtag cagtgacaca gaagcagcaa caccagaatt accaacattc | 3180 |
| ttcccttccc ttgaaaaact tagactttgg tatctggaaa agttgaaggg tttggggaac | 3240 |
| aggagaccga gtagttttcc ccgcctctct gaattggaaa tctgggaatg cccagatcta | 3300 |
| acgtggttc ctccttgtcc aagccttaaa acgttgaaat tggaaaaaaa caatgaagcg | 3360 |
| ttgcaaataa tagtaaaaat aacaacaaca agaggtaaag aagaaaaaga agaagacaag | 3420 |
| aatgctggtg ttggaaattc acaagatgat gacaatgtca aattacgaa ggtgaaata | 3480 |
| gacaatgtga gttatctcaa atcactgccc acaaattgtc ttactcacct caaaataact | 3540 |
| ggaatagatt acagggaggg ggagattgaa tcagattccg tggaggagga gattgaattg | 3600 |
| gaagttgggg aggcatttca gaagtgtgca tcttctttga gaagcctcat cataatcgga | 3660 |
| aatcacggaa taaataaagt gatgagactg tctggaagaa cagggttgga gcatttcact | 3720 |
| ctgttggact cactcaaatt ttcaaagata gaagaccagg aagatgaggg cgaagacaac | 3780 |
| atcatattct ggaaatcctt tcctcaaaac cttcgcagtt tgagaattaa agactctgac | 3840 |
| aaaatgacaa gtttgcccat ggggatgcag tacttaacct ccctccaaac cctcgaacta | 3900 |
| tcatattgtg atgaattgaa ttcccttcca gaatggataa gcagcttatc atctcttcaa | 3960 |
| tacctgcgca tatactactg tccagccctg aaatcactac cagaagcaat gcggaacctc | 4020 |
| acctcccttc agacacttgg gatatcggat tgtccagacc tagttaaaag atgcagaaaa | 4080 |
| cccaacggca aggactatcc caaaattcaa cacatcccca aaattgtact aaatgaatat | 4140 |
| tggtga | 4146 |

<210> SEQ ID NO 3
<211> LENGTH: 4179
<212> TYPE: DNA
<213> ORGANISM: Spinacia oleracea

<400> SEQUENCE: 3

| | |
|---|---:|
| atggccgaaa tcggatactc ggtttgtgcg aaactcatcg aagtgattgg cagtgagctg | 60 |
| atcaaagaga tttgtgacac atgggggttac aaatctcttc ttgaggacct caacaaaact | 120 |
| gtattgacgg tcaggaacgt tctcattcaa gccggggtga tgcggagct tactagtgaa | 180 |

```
caacaaggtt tcattgcaga ccttaaagat gttgtttatg atgctgatga cttgttcgac      240
aagttactca ctcgtgctga gcgaaaacag attgatggaa acgaaatctc tgaaaaggta      300
cgtcgtttct tttcctctag taacaagatc ggtcaagctt actacatgtc tcgtaaggtt      360
aaggaaatta agaagcagtt ggatgaaatt gttgataggc atacaaaatt tgggtttagt      420
gccgagttta tacctgtttg tagggaaagg gggaacgaga gggaaacacg ttcatatata      480
gatgtcaaga atattcttgg gagggataaa gataagaatg atatcataga taggttgctt      540
aatcgtaatg gtaatgaagc ttgtagtttc ctgaccatag tgggagcggg aggattggga      600
aaaactgctc ttgcacaact tgtgttcaat gatgaaaggg tcaaaattga gttccatgat      660
ttgaggtatt gggtttgtgt ctctgatcaa gatgggggcc aatttgatgt gaaagaaatc      720
ctttgtaaga ttttagaggt ggttactaag gagaaagttg ataatagttc acattggaa      780 ttggtacaaa gccaatttca agagaagtta agaggaaaga agtacttcct tgttcttgat      840
gatgtatgga acgaagatcg tgagaagtgg cttcctttgg aagagttgtt aatgttgggt      900 caaggggaa gcaaggttgt agtgaccgca cgttcagaga agacagcaaa tgtcataggg      960
aaaagacatt tttatacact ggaatgtttg tcaccagatt attcatggag cttatttgaa     1020
atgtcggctt tcagaaagg gcatgagcag gaaaaccatc acgaactagt tgatattggg     1080
aaaaagattg ttgaaaaatg ttataacaat ccacttgcta taacggtggt aggaagtctt     1140
ctttatggag aggagataag taagtggcgg tcatttgaaa tgagtgagtt ggccaaaatt     1200
ggcaatgggg ataataagat tttgccgata ttaaagctca gttaccataa tcttataccc     1260
tcgttgaaga gttgcttcag ttattgtgca gtgtttccca aggatcatga aataaagaag     1320
gagatgttga ttgatctttg gatagcacaa ggatacgttg tggcacttga tggaggtcaa     1380
agtatagaag atgctgccga agaacatttt gtaattttgt tacggagatg tttctttcaa     1440
gatgtaaaga aggatgaata tggtgatgtt gattctgtta aaatccacga cttgatgcac     1500
gatgtcgccc aagaagtggg gagggaggaa atatgtgtag tgaatgataa tacaaagaac     1560
ttgggtgata aaatccgtca tgtacatggt gatgtcaata gatatgcaca aagagtctct     1620
ctgtgtagcc atagccataa gattcgttcg tatattggtg gtgattgtga aaaacgttgt     1680
gtggatacac taatagacaa gtggatgtgt cttaggatgt tggacttgtc atggtcggat     1740
gttaaaaatt tgcctaattc aataggtaaa ttgttgcact tgaggtatct taacctgtca     1800
gataatagaa atctaaagat acttcctgat gcaattacaa gactgcataa tttgcagaca     1860
ctgcttttag aagattgcag aagtttaaag gagttgccaa aagattttg caaattggtc     1920 aaactgaggc acttggaatt acagggttgt catgatttga ttggtatgcc atttggaatg     1980
gataagctaa ctagtcttag aatactacca aacattgtgg tgggtaggaa ggaacaaagt     2040
gatgatgagc tgaaagccct aaaaggcctc accgagataa aaggctccat ttctatcaga     2100
atctattcaa agtatagaat agttgaaggc atgaatgaca caggaggagc tgcttatttg     2160
aagagcatga acatctcag ggagattgat attacatttt tgggtgaatg tgttggccct     2220
gaagctgtat tggaaacctt agagccacct tcaaatatca agagcttata tatatataat     2280
tacagtggta caacaattcc agtatgggga agagcagaga ttaattgggc aatctccctc     2340
tcacatctcg tcgacatcca gcttagttgt tgtagtaatt tgcaggagat gccagtgctg     2400
agtaaactgc tcatttgaa atcgctgaaa cttggatggt tggataactt agagtacatg     2460
gagagtagca gtagcagtga cacagaagca gcaacaccag aattaccaac attcttccct     2520
tcccttgaaa aacttacttt acagcatctg gaaaagttga agggttttgg gaacaggaga     2580
```

-continued

```
tcgagtagtt ttccccgcct ctctgaattg gaaatcaaga aatgcccaga tctaacgtca      2640
tttccttctt gtccaagcct tgagaagttg gaattgaaaa aaagcaatga agcattgcaa      2700
ataatagtaa aaataacaac aagaggtaaa gaaaagaag agaacaataa tgctggtgtt       2760
agaaattcac aagatgatga caaagtcaaa ttacggaaga tggtgataga caatctgggt     2820
tatctcacgg gggttgatat tagatttgat gatagagaag gtggatttgt taaccctgaa     2880
gctgtgttgg caaccctaga gccaccttca aatatcaaga gcttatctat acatcgtttt    2940
gatggtaaaa cacttccagt atggggaaga gcagagatta ttgggcaat ctccctctca    3000 catcttgtcg acatccagct ttggcattgt cgtaatttgc aggagatgcc agtgctgagt     3060
aaactgcctc atttgaaatc actggaactt tataatttga ttagtttaga gtacatggag     3120
agcacaagca gaagcagtag cagtgacaca gaagcagcaa caccagaatt accaacattc    3180
ttcccttccc ttgaaaaact tagactttgg tatctggaaa agttgaaggg tttggggaac    3240
aggagaccga gtagttttcc ccgcctctct gaattgaaaa tctgggaatg cccagatcta    3300
acgtggtttc ctccttgtcc aagccttaaa acgttgaaat tggaaaaaaa caatgaagcg    3360
ttgcaaataa tagtaaaaat aacaacaaca agaggtaaag aagaaaaaga agaagacaag    3420
aatgctggtg ttggaaattc acaagatgat gacaatgtca aattacggaa ggtggaaata    3480
gacaatgtga gttatctcaa atcactgccc acaaattgtc ttactcacct caaaataact    3540
ggaatagatt acagggaggg ggagattgaa tcagattccg tggaggagga gattgaattg    3600
gaagttgggg aggcatttca gaagtgtgca tcttcttga gaagcctcat cataatcgga    3660
aatcacggaa taaataaagt gatgagactg tctggaagaa cagggttgga gcatttcact    3720
ctgttggact cactcaaatt ttcaaagata gaagaccagg aagatgaggg cgaagacaac    3780
atcatattct ggaaatcctt tcctcaaaac cttcgcagtt tgagaattaa agactctgac    3840
aaaatgacaa gtttgcccat ggggatgcag tacttaacct ccctccaaac cctcgaacta    3900
tcatattgtg atgaattgaa ttcccttcca gaatggataa gcagcttatc atctcttcaa    3960
tacctgcgca tatactactg tccagccctg aaatcactac cagaagcaat gcggaacctc    4020
acctcccttc agacacttgg gatatcggat tgtccagacc tagttaaaag atgcagaaaa    4080
cccaacggca aggactatcc caaaattcaa cacatcccca aaattttact caacactagc    4140
ttgatcctga acgcacccaa ccttcaggac atggattga                           4179
```

<210> SEQ ID NO 4
<211> LENGTH: 1381
<212> TYPE: PRT
<213> ORGANISM: Spinacia oleracea

<400> SEQUENCE: 4

```
Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30

Leu Leu Glu Asp Leu Asn Lys Thr Val Leu Thr Val Arg Asn Val Leu
        35                  40                  45

Ile Gln Ala Gly Val Met Arg Glu Leu Thr Ser Glu Gln Gln Gly Phe
    50                  55                  60

Ile Ala Asp Leu Lys Asp Val Val Tyr Asp Ala Asp Asp Leu Phe Asp
65                  70                  75                  80

Lys Leu Leu Thr Arg Ala Glu Arg Lys Gln Ile Asp Gly Asn Glu Ile
```

-continued

```
                85                  90                  95
Ser Glu Lys Val Arg Phe Phe Ser Ser Asn Lys Ile Gly Gln
                100                 105                 110
Ala Tyr Tyr Met Ser Arg Lys Val Lys Glu Ile Lys Lys Gln Leu Asp
                115                 120                 125
Glu Ile Val Asp Arg His Thr Lys Phe Gly Phe Ser Ala Glu Phe Ile
130                 135                 140
Pro Val Cys Arg Glu Arg Gly Asn Glu Arg Thr Arg Ser Tyr Ile
145                 150                 155                 160
Asp Val Lys Asn Ile Leu Gly Arg Asp Lys Asp Lys Asn Asp Ile Ile
                165                 170                 175
Asp Arg Leu Leu Asn Arg Asn Gly Asn Glu Ala Cys Ser Phe Leu Thr
                180                 185                 190
Ile Val Gly Ala Gly Gly Leu Gly Lys Thr Ala Leu Ala Gln Leu Val
                195                 200                 205
Phe Asn Asp Glu Arg Val Lys Ile Glu Phe His Asp Leu Arg Tyr Trp
210                 215                 220
Val Cys Val Ser Asp Gln Asp Gly Gly Gln Phe Asp Val Lys Glu Ile
225                 230                 235                 240
Leu Cys Lys Ile Leu Glu Val Val Thr Lys Glu Lys Val Asp Asn Ser
                245                 250                 255
Ser Thr Leu Glu Leu Val Gln Ser Gln Phe Gln Glu Lys Leu Arg Gly
                260                 265                 270
Lys Lys Tyr Phe Leu Val Leu Asp Asp Val Trp Asn Glu Asp Arg Glu
                275                 280                 285
Lys Trp Leu Pro Leu Glu Glu Leu Met Leu Gly Gln Gly Gly Ser
                290                 295                 300
Lys Val Val Val Thr Ala Arg Ser Glu Lys Thr Ala Asn Val Ile Gly
305                 310                 315                 320
Lys Arg His Phe Tyr Thr Leu Glu Cys Leu Ser Pro Asp Tyr Ser Trp
                325                 330                 335
Ser Leu Phe Glu Met Ser Ala Phe Gln Lys Gly His Glu Gln Glu Asn
                340                 345                 350
His His Glu Leu Val Asp Ile Gly Lys Lys Ile Val Glu Lys Cys Tyr
                355                 360                 365
Asn Asn Pro Leu Ala Ile Thr Val Val Gly Ser Leu Leu Tyr Gly Glu
                370                 375                 380
Glu Ile Ser Lys Trp Arg Ser Phe Glu Met Ser Glu Leu Ala Lys Ile
385                 390                 395                 400
Gly Asn Gly Asp Asn Lys Ile Leu Pro Ile Leu Lys Leu Ser Tyr His
                405                 410                 415
Asn Leu Ile Pro Ser Leu Lys Ser Cys Phe Ser Tyr Cys Ala Val Phe
                420                 425                 430
Pro Lys Asp His Glu Ile Lys Lys Glu Met Leu Ile Asp Leu Trp Ile
                435                 440                 445
Ala Gln Gly Tyr Val Val Ala Leu Asp Gly Gly Gln Ser Ile Glu Asp
                450                 455                 460
Ala Ala Glu Glu His Phe Val Ile Leu Leu Arg Arg Cys Phe Phe Gln
465                 470                 475                 480
Asp Val Lys Lys Asp Glu Tyr Gly Asp Val Asp Ser Val Lys Ile His
                485                 490                 495
Asp Leu Met His Asp Val Ala Gln Glu Val Gly Arg Glu Glu Ile Cys
                500                 505                 510
```

```
Val Val Asn Asp Asn Thr Lys Asn Leu Gly Asp Lys Ile Arg His Val
            515                 520                 525

His Gly Asp Val Asn Arg Tyr Ala Gln Arg Val Ser Leu Cys Ser His
    530                 535                 540

Ser His Lys Ile Arg Ser Tyr Ile Gly Gly Asp Cys Glu Lys Arg Cys
545                 550                 555                 560

Val Asp Thr Leu Ile Asp Lys Trp Met Cys Leu Arg Met Leu Asp Leu
                565                 570                 575

Ser Trp Ser Asp Val Lys Asn Leu Pro Asn Ser Ile Gly Lys Leu Leu
            580                 585                 590

His Leu Arg Tyr Leu Asn Leu Ser Asp Asn Arg Asn Leu Lys Ile Leu
        595                 600                 605

Pro Asp Ala Ile Thr Arg Leu His Asn Leu Gln Thr Leu Leu Leu Glu
    610                 615                 620

Asp Cys Arg Ser Leu Lys Glu Leu Pro Lys Asp Phe Cys Lys Leu Val
625                 630                 635                 640

Lys Leu Arg His Leu Glu Leu Gln Gly Cys His Asp Leu Ile Gly Met
                645                 650                 655

Pro Phe Gly Met Asp Lys Leu Thr Ser Leu Arg Ile Leu Pro Asn Ile
            660                 665                 670

Val Val Gly Arg Lys Glu Gln Ser Asp Asp Glu Leu Lys Ala Leu Lys
        675                 680                 685

Gly Leu Thr Glu Ile Lys Gly Ser Ile Ser Ile Arg Ile Tyr Ser Lys
    690                 695                 700

Tyr Arg Ile Val Glu Gly Met Asn Asp Thr Gly Gly Ala Ala Tyr Leu
705                 710                 715                 720

Lys Ser Met Lys His Leu Arg Glu Ile Asp Ile Thr Phe Leu Gly Glu
                725                 730                 735

Cys Val Gly Pro Glu Ala Val Leu Glu Thr Leu Glu Pro Pro Ser Asn
            740                 745                 750

Ile Lys Ser Leu Tyr Ile Tyr Asn Tyr Ser Gly Thr Thr Ile Pro Val
        755                 760                 765

Trp Gly Arg Ala Glu Ile Asn Trp Ala Ile Ser Leu Ser His Leu Val
    770                 775                 780

Asp Ile Gln Leu Ser Cys Cys Ser Asn Leu Gln Glu Met Pro Val Leu
785                 790                 795                 800

Ser Lys Leu Pro His Leu Lys Ser Leu Lys Leu Gly Trp Leu Asp Asn
                805                 810                 815

Leu Glu Tyr Met Glu Ser Ser Ser Ser Asp Thr Glu Ala Ala Thr
            820                 825                 830

Pro Glu Leu Pro Thr Phe Phe Pro Ser Leu Glu Lys Leu Thr Leu Gln
        835                 840                 845

His Leu Glu Lys Leu Lys Gly Phe Gly Asn Arg Arg Ser Ser Ser Phe
    850                 855                 860

Pro Arg Leu Ser Glu Leu Glu Ile Lys Lys Cys Pro Asp Leu Thr Ser
865                 870                 875                 880

Phe Pro Ser Cys Pro Ser Leu Glu Lys Leu Glu Leu Lys Glu Ser Asn
                885                 890                 895

Glu Ala Leu Gln Ile Ile Val Lys Ile Thr Thr Arg Gly Lys Glu Lys
            900                 905                 910

Glu Glu Asn Asn Asn Ala Gly Val Arg Asn Ser Gln Asp Asp Lys
        915                 920                 925
```

```
Val Lys Leu Arg Lys Met Val Ile Asp Asn Leu Gly Tyr Leu Thr Gly
    930                 935                 940
Val Asp Ile Arg Phe Asp Asp Arg Glu Gly Gly Phe Val Asn Pro Glu
945                 950                 955                 960
Ala Val Leu Ala Thr Leu Glu Pro Pro Ser Asn Ile Lys Ser Leu Ser
                965                 970                 975
Ile His Arg Phe Asp Gly Lys Thr Leu Pro Val Trp Gly Arg Ala Glu
                980                 985                 990
Ile Asn Trp Ala Ile Ser Leu Ser His Leu Val Asp Ile Gln Leu Trp
        995                 1000                1005
His Cys Arg Asn Leu Gln Glu Met Pro Val Leu Ser Lys Leu Pro His
    1010                1015                1020
Leu Lys Ser Leu Glu Leu Tyr Asn Leu Ile Ser Leu Glu Tyr Met Glu
1025                1030                1035                1040
Ser Thr Ser Arg Ser Ser Ser Asp Thr Glu Ala Ala Thr Pro Glu
                1045                1050                1055
Leu Pro Thr Phe Phe Pro Ser Leu Glu Lys Leu Arg Leu Trp Tyr Leu
            1060                1065                1070
Glu Lys Leu Lys Gly Leu Gly Asn Arg Arg Pro Ser Ser Phe Pro Arg
        1075                1080                1085
Leu Ser Glu Leu Glu Ile Trp Glu Cys Pro Asp Leu Thr Trp Phe Pro
    1090                1095                1100
Pro Cys Pro Ser Leu Lys Thr Leu Lys Leu Glu Lys Asn Asn Glu Ala
1105                1110                1115                1120
Leu Gln Ile Ile Val Lys Ile Thr Thr Thr Arg Gly Lys Glu Glu Lys
                1125                1130                1135
Glu Glu Asp Lys Asn Ala Gly Val Gly Asn Ser Gln Asp Asp Asn
            1140                1145                1150
Val Lys Leu Arg Lys Val Glu Ile Asp Asn Val Ser Tyr Leu Lys Ser
        1155                1160                1165
Leu Pro Thr Asn Cys Leu Thr His Leu Lys Ile Thr Gly Ile Asp Tyr
    1170                1175                1180
Arg Glu Gly Glu Ile Glu Ser Asp Ser Val Glu Glu Glu Ile Glu Leu
1185                1190                1195                1200
Glu Val Gly Glu Ala Phe Gln Lys Cys Ala Ser Ser Leu Arg Ser Leu
                1205                1210                1215
Ile Ile Ile Gly Asn His Gly Ile Asn Lys Val Met Arg Leu Ser Gly
                1220                1225                1230
Arg Thr Gly Leu Glu His Phe Thr Leu Leu Asp Ser Leu Lys Phe Ser
            1235                1240                1245
Lys Ile Glu Asp Gln Glu Asp Glu Gly Glu Asp Asn Ile Ile Phe Trp
    1250                1255                1260
Lys Ser Phe Pro Gln Asn Leu Arg Ser Leu Arg Ile Lys Asp Ser Asp
1265                1270                1275                1280
Lys Met Thr Ser Leu Pro Met Gly Met Gln Tyr Leu Thr Ser Leu Gln
                1285                1290                1295
Thr Leu Glu Leu Ser Tyr Cys Asp Glu Leu Asn Ser Leu Pro Glu Trp
            1300                1305                1310
Ile Ser Ser Leu Ser Ser Leu Gln Tyr Leu Arg Ile Tyr Tyr Cys Pro
    1315                1320                1325
Ala Leu Lys Ser Leu Pro Glu Ala Met Arg Asn Leu Thr Ser Leu Gln
    1330                1335                1340
Thr Leu Gly Ile Ser Asp Cys Pro Asp Leu Val Lys Arg Cys Arg Lys
```

-continued

```
1345                1350                1355                1360
Pro Asn Gly Lys Asp Tyr Pro Lys Ile Gln His Ile Pro Lys Ile Val
                1365                1370                1375
Leu Asn Glu Tyr Trp
            1380

<210> SEQ ID NO 5
<211> LENGTH: 1392
<212> TYPE: PRT
<213> ORGANISM: Spinacia oleracea

<400> SEQUENCE: 5

Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30

Leu Leu Glu Asp Leu Asn Lys Thr Val Leu Thr Val Arg Asn Val Leu
        35                  40                  45

Ile Gln Ala Gly Val Met Arg Glu Leu Thr Ser Glu Gln Gln Gly Phe
    50                  55                  60

Ile Ala Asp Leu Lys Asp Val Val Tyr Asp Ala Asp Asp Leu Phe Asp
65                  70                  75                  80

Lys Leu Leu Thr Arg Ala Glu Arg Lys Gln Ile Asp Gly Asn Glu Ile
                85                  90                  95

Ser Glu Lys Val Arg Arg Phe Phe Ser Ser Ser Asn Lys Ile Gly Gln
            100                 105                 110

Ala Tyr Tyr Met Ser Arg Lys Val Lys Glu Ile Lys Lys Gln Leu Asp
        115                 120                 125

Glu Ile Val Asp Arg His Thr Lys Phe Gly Phe Ser Ala Glu Phe Ile
    130                 135                 140

Pro Val Cys Arg Glu Arg Gly Asn Glu Arg Glu Thr Arg Ser Tyr Ile
145                 150                 155                 160

Asp Val Lys Asn Ile Leu Gly Arg Asp Lys Asp Lys Asn Asp Ile Ile
                165                 170                 175

Asp Arg Leu Leu Asn Arg Asn Gly Asn Glu Ala Cys Ser Phe Leu Thr
            180                 185                 190

Ile Val Gly Ala Gly Gly Leu Gly Lys Thr Ala Leu Ala Gln Leu Val
        195                 200                 205

Phe Asn Asp Glu Arg Val Lys Ile Glu Phe His Asp Leu Arg Tyr Trp
    210                 215                 220

Val Cys Val Ser Asp Gln Asp Gly Gln Phe Asp Val Lys Glu Ile
225                 230                 235                 240

Leu Cys Lys Ile Leu Glu Val Val Thr Lys Glu Lys Val Asp Asn Ser
                245                 250                 255

Ser Thr Leu Glu Leu Val Gln Ser Gln Phe Gln Glu Lys Leu Arg Gly
            260                 265                 270

Lys Lys Tyr Phe Leu Val Leu Asp Asp Val Trp Asn Glu Asp Arg Glu
        275                 280                 285

Lys Trp Leu Pro Leu Glu Glu Leu Leu Met Leu Gly Gln Gly Gly Ser
    290                 295                 300

Lys Val Val Val Thr Ala Arg Ser Glu Lys Thr Ala Asn Val Ile Gly
305                 310                 315                 320

Lys Arg His Phe Tyr Thr Leu Glu Cys Leu Ser Pro Asp Tyr Ser Trp
                325                 330                 335
```

```
Ser Leu Phe Glu Met Ser Ala Phe Gln Lys Gly His Glu Gln Glu Asn
                340                 345                 350

His His Glu Leu Val Asp Ile Gly Lys Lys Ile Val Gly Lys Cys Tyr
            355                 360                 365

Asn Asn Pro Leu Ala Ile Thr Val Val Gly Ser Leu Leu Tyr Gly Glu
    370                 375                 380

Glu Ile Ser Lys Trp Arg Ser Phe Glu Met Ser Glu Leu Ala Lys Ile
385                 390                 395                 400

Gly Asn Gly Asp Asn Lys Ile Leu Pro Ile Leu Lys Leu Ser Tyr His
                405                 410                 415

Asn Leu Ile Pro Ser Leu Lys Ser Cys Phe Ser Tyr Cys Ala Val Phe
            420                 425                 430

Pro Lys Asp His Glu Ile Lys Lys Glu Met Leu Ile Asp Leu Trp Ile
    435                 440                 445

Ala Gln Gly Tyr Val Val Ala Leu Asp Gly Gly Gln Ser Ile Glu Asp
    450                 455                 460

Ala Ala Glu Glu His Phe Val Ile Leu Leu Arg Arg Cys Phe Phe Gln
465                 470                 475                 480

Asp Val Lys Lys Asp Glu Tyr Gly Asp Val Asp Ser Val Lys Ile His
                485                 490                 495

Asp Leu Met His Asp Val Ala Gln Glu Val Gly Arg Glu Glu Ile Cys
            500                 505                 510

Val Val Asn Asp Asn Thr Lys Asn Leu Gly Asp Lys Ile Arg His Val
    515                 520                 525

His Gly Asp Val Asn Arg Tyr Ala Gln Arg Val Ser Leu Cys Ser His
    530                 535                 540

Ser His Lys Ile Arg Ser Tyr Ile Gly Gly Asp Cys Glu Lys Arg Cys
545                 550                 555                 560

Val Asp Thr Leu Ile Asp Lys Trp Met Cys Leu Arg Met Leu Asp Leu
            565                 570                 575

Ser Trp Ser Asp Val Lys Asn Leu Pro Asn Ser Ile Gly Lys Leu Leu
            580                 585                 590

His Leu Arg Tyr Leu Asn Leu Ser Asp Asn Arg Asn Leu Lys Ile Leu
            595                 600                 605

Pro Asp Ala Ile Thr Arg Leu His Asn Leu Gln Thr Leu Leu Leu Glu
    610                 615                 620

Asp Cys Arg Ser Leu Lys Glu Leu Pro Lys Asp Phe Cys Lys Leu Val
625                 630                 635                 640

Lys Leu Arg His Leu Glu Leu Gln Gly Cys His Asp Leu Ile Gly Met
                645                 650                 655

Pro Phe Gly Met Asp Lys Leu Thr Ser Leu Arg Ile Leu Pro Asn Ile
            660                 665                 670

Val Val Gly Arg Lys Glu Gln Ser Asp Asp Glu Leu Lys Ala Leu Lys
    675                 680                 685

Gly Leu Thr Glu Ile Lys Gly Ser Ile Ser Ile Arg Ile Tyr Ser Lys
    690                 695                 700

Tyr Arg Ile Val Glu Gly Met Asn Asp Thr Gly Gly Ala Ala Tyr Leu
705                 710                 715                 720

Lys Ser Met Lys His Leu Arg Glu Ile Asp Ile Thr Phe Leu Gly Glu
                725                 730                 735

Cys Val Gly Pro Glu Ala Val Leu Glu Thr Leu Glu Pro Pro Ser Asn
            740                 745                 750

Ile Lys Ser Leu Tyr Ile Tyr Asn Tyr Ser Gly Thr Thr Ile Pro Val
```

```
                755                 760                 765
Trp Gly Arg Ala Glu Ile Asn Trp Ala Ile Ser Leu Ser His Leu Val
    770                 775                 780

Asp Ile Gln Leu Ser Cys Cys Ser Asn Leu Gln Glu Met Pro Val Leu
785                 790                 795                 800

Ser Lys Leu Pro His Leu Lys Ser Leu Lys Leu Gly Trp Leu Asp Asn
                805                 810                 815

Leu Glu Tyr Met Glu Ser Ser Ser Ser Asp Thr Glu Ala Ala Thr
            820                 825                 830

Pro Glu Leu Pro Thr Phe Phe Pro Ser Leu Glu Lys Leu Thr Leu Gln
                835                 840                 845

His Leu Glu Lys Leu Lys Gly Phe Gly Asn Arg Arg Ser Ser Ser Phe
    850                 855                 860

Pro Arg Leu Ser Glu Leu Glu Ile Lys Lys Cys Pro Asp Leu Thr Ser
865                 870                 875                 880

Phe Pro Ser Cys Pro Ser Leu Glu Lys Leu Glu Leu Lys Glu Ser Asn
                885                 890                 895

Glu Ala Leu Gln Ile Ile Val Lys Ile Thr Thr Arg Gly Lys Glu Lys
                900                 905                 910

Glu Glu Asn Asn Asn Ala Gly Val Arg Asn Ser Gln Asp Asp Lys
    915                 920                 925

Val Lys Leu Arg Lys Met Val Ile Asp Asn Leu Gly Tyr Leu Thr Gly
    930                 935                 940

Val Asp Ile Arg Phe Asp Asp Arg Glu Gly Gly Phe Val Asn Pro Glu
945                 950                 955                 960

Ala Val Leu Ala Thr Leu Glu Pro Pro Ser Asn Ile Lys Ser Leu Ser
                965                 970                 975

Ile His Arg Phe Asp Gly Lys Thr Leu Pro Val Trp Gly Arg Ala Glu
            980                 985                 990

Ile Asn Trp Ala Ile Ser Leu Ser His Leu Val Asp Ile Gln Leu Trp
    995                 1000                1005

His Cys Arg Asn Leu Gln Glu Met Pro Val Leu Ser Lys Leu Pro His
    1010                1015                1020

Leu Lys Ser Leu Glu Leu Tyr Asn Leu Ile Ser Leu Glu Tyr Met Glu
1025                1030                1035                1040

Ser Thr Ser Arg Ser Ser Ser Asp Thr Glu Ala Ala Thr Pro Glu
                1045                1050                1055

Leu Pro Thr Phe Phe Pro Ser Leu Glu Lys Leu Arg Leu Trp Tyr Leu
                1060                1065                1070

Glu Lys Leu Lys Gly Leu Gly Asn Arg Arg Pro Ser Ser Phe Pro Arg
    1075                1080                1085

Leu Ser Glu Leu Glu Ile Trp Glu Cys Pro Asp Leu Thr Trp Phe Pro
    1090                1095                1100

Pro Cys Pro Ser Leu Lys Thr Leu Lys Leu Glu Lys Asn Asn Glu Ala
1105                1110                1115                1120

Leu Gln Ile Ile Val Lys Ile Thr Thr Arg Gly Lys Glu Glu Lys
    1125                1130                1135

Glu Glu Asp Lys Asn Ala Gly Val Gly Asn Ser Gln Asp Asp Asn
    1140                1145                1150

Val Lys Leu Arg Lys Val Glu Ile Asp Asn Val Ser Tyr Leu Lys Ser
    1155                1160                1165

Leu Pro Thr Asn Cys Leu Thr His Leu Lys Ile Thr Gly Ile Asp Tyr
    1170                1175                1180
```

-continued

```
Arg Glu Gly Glu Ile Glu Ser Asp Ser Val Glu Glu Ile Glu Leu
1185                1190                1195                1200

Glu Val Gly Glu Ala Phe Gln Lys Cys Ala Ser Ser Leu Arg Ser Leu
            1205                1210                1215

Ile Ile Ile Gly Asn His Gly Ile Asn Lys Val Met Arg Leu Ser Gly
        1220                1225                1230

Arg Thr Gly Leu Glu His Phe Thr Leu Leu Asp Ser Leu Lys Phe Ser
            1235                1240                1245

Lys Ile Glu Asp Gln Glu Asp Glu Gly Glu Asp Asn Ile Ile Phe Trp
        1250                1255                1260

Lys Ser Phe Pro Gln Asn Leu Arg Ser Leu Arg Ile Lys Asp Ser Asp
1265                1270                1275                1280

Lys Met Thr Ser Leu Pro Met Gly Met Gln Tyr Leu Thr Ser Leu Gln
            1285                1290                1295

Thr Leu Glu Leu Ser Tyr Cys Asp Glu Leu Asn Ser Leu Pro Glu Trp
        1300                1305                1310

Ile Ser Ser Leu Ser Ser Leu Gln Tyr Leu Arg Ile Tyr Tyr Cys Pro
        1315                1320                1325

Ala Leu Lys Ser Leu Pro Glu Ala Met Arg Asn Leu Thr Ser Leu Gln
        1330                1335                1340

Thr Leu Gly Ile Ser Asp Cys Pro Asp Leu Val Lys Arg Cys Arg Lys
1345                1350                1355                1360

Pro Asn Gly Lys Asp Tyr Pro Lys Ile Gln His Ile Pro Lys Ile Leu
            1365                1370                1375

Leu Asn Thr Ser Leu Ile Leu Asn Ala Pro Asn Leu Gln Asp Met Asp
        1380                1385                1390

<210> SEQ ID NO 6
<211> LENGTH: 20
<212> TYPE: DNA
<213> ORGANISM: Spinacia oleracea
<220> FEATURE:
<223> OTHER INFORMATION: Primer

<400> SEQUENCE: 6
acaagtggat gtgtcttagg                                                 20

<210> SEQ ID NO 7
<211> LENGTH: 19
<212> TYPE: DNA
<213> ORGANISM: Spinacia oleracea
<220> FEATURE:
<223> OTHER INFORMATION: Primer

<400> SEQUENCE: 7
ttcgccctca tcttcctgg                                                  19

<210> SEQ ID NO 8
<211> LENGTH: 18
<212> TYPE: DNA
<213> ORGANISM: Spinacia oleracea
<220> FEATURE:
<223> OTHER INFORMATION: Primer

<400> SEQUENCE: 8
tcacgtgggt tgtgttgt                                                   18

<210> SEQ ID NO 9
<211> LENGTH: 2078
```

<212> TYPE: DNA
<213> ORGANISM: Spinacia oleracea

<400> SEQUENCE: 9

| | | | | | |
|---|---|---|---|---|---|
| acaagtggat | gtgtcttagg | atgttggact | tgtcatggtc | ggatgttaaa | aatttgccta | 60 |
| attcaatagg | taaattgttg | cacttgaggt | atcttaacct | gtcagataat | agaaatctaa | 120 |
| agatacttcc | tgatgcaatt | acaagactgc | ataatttgca | gacactgctt | ttagaagatt | 180 |
| gcagaagttt | aaaggagttg | ccaaaagatt | tttgcaaatt | ggtcaaactg | aggcacttgg | 240 |
| aattacaggg | ttgtcatgat | ttgattggta | tgccatttgg | aatggataag | ctaactagtc | 300 |
| ttagaatact | accaaacatt | gtggtgggta | ggaaggaaca | aagtgatgat | gagctgaaag | 360 |
| ccctaaaagg | cctcaccgag | ataaaaggct | ccatttctat | cagaatctat | tcaaagtata | 420 |
| gaatagttga | aggcatgaat | gacacaggag | gagctgctta | tttgaagagc | atgaaacatc | 480 |
| tcagggagat | tgatattaca | tttttgggtg | aatgtgttgg | ccctgaagct | gtattggaaa | 540 |
| ccttagagcc | accttcaaat | atcaagagct | tatatatata | taattacagt | ggtacaacaa | 600 |
| ttccagtatg | gggaagagca | gagattaatt | gggcaatctc | cctctcacat | ctcgtcgaca | 660 |
| tccagcttag | ttgttgtagt | aatttgcagg | agatgccagt | gctgagtaaa | ctgcctcatt | 720 |
| tgaaatcgct | gaaacttgga | tggttggata | acttagagta | catggagagt | agcagtagca | 780 |
| gtgacacaga | agcagcaaca | ccagaattac | caacattctt | cccttccctt | gaaaaactta | 840 |
| ctttacagca | tctggaaaag | ttgaagggtt | ttgggaacag | gagatcgagt | agttttcccc | 900 |
| gcctctctga | attggaaatc | aagaaatgcc | cagatctaac | gtcatttcct | tcttgtccaa | 960 |
| gccttgagaa | gttggaattg | aaagaaagca | atgaagcatt | gcaaataata | gtaaaaataa | 1020 |
| caacaagagg | taaagaaaaa | gaagagaaca | ataatgctgg | tgttagaaat | tcacaagatg | 1080 |
| atgacaaagt | caaattacgg | aagatggtga | tagacaatct | gggttatctc | acggggttg | 1140 |
| atattagatt | tgatgataga | gaaggtggat | ttgttaaccc | tgaagctgtg | ttggcaaccc | 1200 |
| tagagccacc | ttcaaatatc | aagagcttat | ctatacatcg | ttttgatggt | aaaacacttc | 1260 |
| cagtatgggg | aagagcagag | attaattggg | caatctccct | ctcacatctt | gtcgacatcc | 1320 |
| agctttggca | ttgtcgtaat | ttgcaggaga | tgccagtgct | gagtaaactg | cctcatttga | 1380 |
| aatcactgga | actttataat | ttgattagtt | tagagtacat | ggagagcaca | agcagaagca | 1440 |
| gtagcagtga | cacagaagca | gcaacaccag | aattaccaac | attcttccct | tcccttgaaa | 1500 |
| aacttagact | ttggtatctg | aaaagttga | agggtttggg | gaacaggaga | ccgagtagtt | 1560 |
| ttccccgcct | ctctgaattg | gaaatctggg | aatgcccaga | tctaacgtgg | tttcctcctt | 1620 |
| gtccaagcct | taaaacgttg | aaattggaaa | aaaacaatga | agcgttgcaa | ataatagtaa | 1680 |
| aaataacaac | aacaagaggt | aaagaagaaa | agaagaagaa | caagaatgct | ggtgttggaa | 1740 |
| attcacaaga | tgatgacaat | gtcaaattac | ggaaggtgga | aatagacaat | gtgagttatc | 1800 |
| tcaaatcact | gcccacaaat | tgtcttactc | acctcaaaat | aactggaata | gattacaggg | 1860 |
| aggggagat | tgaatcagat | tccgtggagg | aggagattga | attggaagtt | ggggaggcat | 1920 |
| ttcagaagtg | tgcatcttct | ttgagaagcc | tcatcataat | cggaaatcac | ggaataaata | 1980 |
| aagtgatgag | actgtctgga | agaacagggt | tggagcattt | cactctgttg | gactcactca | 2040 |
| aattttcaaa | gatagaagac | caggaagatg | agggcgaa | | | 2078 |

<210> SEQ ID NO 10
<211> LENGTH: 692
<212> TYPE: PRT

<213> ORGANISM: Spinacia oleracea

<400> SEQUENCE: 10

Lys Trp Met Cys Leu Arg Met Leu Asp Leu Ser Trp Ser Asp Val Lys
1               5                   10                  15

Asn Leu Pro Asn Ser Ile Gly Lys Leu Leu His Leu Arg Tyr Leu Asn
            20                  25                  30

Leu Ser Asp Asn Arg Asn Leu Lys Ile Leu Pro Asp Ala Ile Thr Arg
        35                  40                  45

Leu His Asn Leu Gln Thr Leu Leu Glu Asp Cys Arg Ser Leu Lys
    50                  55                  60

Glu Leu Pro Lys Asp Phe Cys Lys Leu Val Lys Leu Arg His Leu Glu
65                  70                  75                  80

Leu Gln Gly Cys His Asp Leu Ile Gly Met Pro Phe Gly Met Asp Lys
                85                  90                  95

Leu Thr Ser Leu Arg Ile Leu Pro Asn Ile Val Val Gly Arg Lys Glu
            100                 105                 110

Gln Ser Asp Asp Glu Leu Lys Ala Leu Lys Gly Leu Thr Glu Ile Lys
            115                 120                 125

Gly Ser Ile Ser Ile Arg Ile Tyr Ser Lys Tyr Arg Ile Val Glu Gly
130                 135                 140

Met Asn Asp Thr Gly Gly Ala Ala Tyr Leu Lys Ser Met Lys His Leu
145                 150                 155                 160

Arg Glu Ile Asp Ile Thr Phe Leu Gly Glu Cys Val Gly Pro Glu Ala
                165                 170                 175

Val Leu Glu Thr Leu Glu Pro Pro Ser Asn Ile Lys Ser Leu Tyr Ile
            180                 185                 190

Tyr Asn Tyr Ser Gly Thr Thr Ile Pro Val Trp Gly Arg Ala Glu Ile
            195                 200                 205

Asn Trp Ala Ile Ser Leu Ser His Leu Val Asp Ile Gln Leu Ser Cys
210                 215                 220

Cys Ser Asn Leu Gln Glu Met Pro Val Leu Ser Lys Leu Pro His Leu
225                 230                 235                 240

Lys Ser Leu Lys Leu Gly Trp Leu Asp Asn Leu Glu Tyr Met Glu Ser
                245                 250                 255

Ser Ser Ser Ser Asp Thr Glu Ala Ala Thr Pro Glu Leu Pro Thr Phe
            260                 265                 270

Phe Pro Ser Leu Glu Lys Leu Thr Leu Gln His Leu Glu Lys Leu Lys
        275                 280                 285

Gly Phe Gly Asn Arg Arg Ser Ser Phe Pro Arg Leu Ser Glu Leu
        290                 295                 300

Glu Ile Lys Lys Cys Pro Asp Leu Thr Ser Phe Pro Ser Cys Pro Ser
305                 310                 315                 320

Leu Glu Lys Leu Glu Leu Lys Glu Ser Asn Glu Ala Leu Gln Ile Ile
            325                 330                 335

Val Lys Ile Thr Thr Arg Gly Lys Lys Glu Glu Asn Asn Ala
        340                 345                 350

Gly Val Arg Asn Ser Gln Asp Asp Lys Val Lys Leu Arg Lys Met
            355                 360                 365

Val Ile Asp Asn Leu Gly Tyr Leu Thr Gly Val Asp Ile Arg Phe Asp
        370                 375                 380

Asp Arg Glu Gly Gly Phe Val Asn Pro Glu Ala Val Leu Ala Thr Leu
385                 390                 395                 400

```
Glu Pro Pro Ser Asn Ile Lys Ser Leu Ser Ile His Arg Phe Asp Gly
                405                 410                 415

Lys Thr Leu Pro Val Trp Gly Arg Ala Glu Ile Asn Trp Ala Ile Ser
            420                 425                 430

Leu Ser His Leu Val Asp Ile Gln Leu Trp His Cys Arg Asn Leu Gln
        435                 440                 445

Glu Met Pro Val Leu Ser Lys Leu Pro His Leu Lys Ser Leu Glu Leu
    450                 455                 460

Tyr Asn Leu Ile Ser Leu Glu Tyr Met Glu Ser Thr Ser Arg Ser Ser
465                 470                 475                 480

Ser Ser Asp Thr Glu Ala Ala Thr Pro Glu Leu Pro Thr Phe Phe Pro
            485                 490                 495

Ser Leu Glu Lys Leu Arg Leu Trp Tyr Leu Glu Lys Leu Lys Gly Leu
        500                 505                 510

Gly Asn Arg Arg Pro Ser Ser Phe Pro Arg Leu Ser Glu Leu Glu Ile
    515                 520                 525

Trp Glu Cys Pro Asp Leu Thr Trp Phe Pro Pro Cys Pro Ser Leu Lys
530                 535                 540

Thr Leu Lys Leu Glu Lys Asn Asn Glu Ala Leu Gln Ile Ile Val Lys
545                 550                 555                 560

Ile Thr Thr Thr Arg Gly Lys Glu Lys Glu Glu Asp Lys Asn Ala
            565                 570                 575

Gly Val Gly Asn Ser Gln Asp Asp Asn Val Lys Leu Arg Lys Val
        580                 585                 590

Glu Ile Asp Asn Val Ser Tyr Leu Lys Ser Leu Pro Thr Asn Cys Leu
    595                 600                 605

Thr His Leu Lys Ile Thr Gly Ile Asp Tyr Arg Glu Gly Glu Ile Glu
    610                 615                 620

Ser Asp Ser Val Glu Glu Ile Glu Leu Glu Val Gly Glu Ala Phe
625                 630                 635                 640

Gln Lys Cys Ala Ser Ser Leu Arg Ser Leu Ile Ile Gly Asn His
            645                 650                 655

Gly Ile Asn Lys Val Met Arg Leu Ser Gly Arg Thr Gly Leu Glu His
        660                 665                 670

Phe Thr Leu Leu Asp Ser Leu Lys Phe Ser Lys Ile Glu Asp Gln Glu
    675                 680                 685

Asp Glu Gly Glu
    690

<210> SEQ ID NO 11
<211> LENGTH: 1597
<212> TYPE: DNA
<213> ORGANISM: Spinacia oleracea

<400> SEQUENCE: 11
tcacgtgggt tgtgttgtcg atagagatcc agaaatagtc ttttatgta gcaataagat     60 tcgttcgtat attagcggtc gctgcataaa gaatccggtg gattcacaaa tagacaactg    120
gatgtgcctt agggtgttgg acttgtcaga ttcatgtgtt aaagatttgt ctgattcaat    180
aggtaagctg ctgcacttaa ggtatcttaa cctctcttct aatataaagt tggagataat    240
ccctgatgca attacaagac tgcataactt gcagacacta cttttagaag attgcagaag    300
tttaaaggag ttgccaaaag attttttgcaa attggtcaaa ctgaggcact tggaattaca    360
gggttgtcat gatttgattg gtatgtcatt tggaatggat aagctaacta gtcttagaat    420
```

```
actaccaaac attgtggtgg gtaggaagga acaaagtgtt gatgatgagc tgaaagccct      480
aaaaggcctc accgagataa aaggctccat tgatatcaca atctattcaa aatatagaag      540
agttgaaggc atgaatggca caggaggagg agctgggtat ttgaagagca tgaaacatct      600
cacgggggtt aatattacat ttgatgaagg tggatgtgtt aaccctgaag ctgtgtattt      660
gaagagcatg aaacatctca cgagggttat tattatattt gattataaag gtggatgtgt      720
taaccctgaa gctgtgttgg caaccctaga gccaccttca aatatcaaga ggttagagat      780
gtggcattac agtggtacaa caattccagt atggggaaga gcagagatta attgggcaat      840
ctccctctca catcttgtcg acatcacgct tgaagattgt tacaatttgc aggagatgcc      900
agtgctgagt aaactgcctc atttgaaatc actggaactt acagagttgg ataacttaga      960
gtacatggag agtagaagca gcagcagtag cagtgacaca gaagcagcaa caccagaatt     1020
accaacattc ttcccttccc ttgaaaaact tacactttgg cgtctggaca agttgaaggg     1080
ttttgggaac aggagatcga gtagttttcc ccgcctctct aaattggaaa tctggaaatg     1140
tccagatcta acgtcatttc cttcttgtcc aagccttgaa gagttggaat tgaaagaaaa     1200
caatgaagcg ttgcaaataa tagtaaaaat aacaacaaca agaggtaaag aagaaaaaga     1260
agaagacaag aatgctggtg ttggaaattc acaagatgat gacaatgtca aattatggaa     1320
ggtggaaata gacaatctgg gttatctcaa atcactgccc acaaattgtc tgactcacct     1380
cgaccttaca ataagtgatt ccaaggaggg ggagggtgaa tgggaagttg gggatgcatt     1440
tcagaagtgt gtatcttctt tgagaagcct caccataatc ggaaatcacg gaataaataa     1500
agtgaagaga ctgtctggaa gaacagggtt ggagcatttc actctgttgg aatcactcaa     1560
actttcagat atagaagacc aggaagatga gggcgaa                              1597
```

<210> SEQ ID NO 12
<211> LENGTH: 532
<212> TYPE: PRT
<213> ORGANISM: Spinacia oleracea

<400> SEQUENCE: 12

```
His Val Gly Cys Val Val Asp Arg Asp Pro Glu Ile Val Phe Leu Cys
1               5                   10                  15

Ser Asn Lys Ile Arg Ser Tyr Ile Ser Gly Arg Cys Ile Lys Asn Pro
            20                  25                  30

Val Asp Ser Gln Ile Asp Asn Trp Met Cys Leu Arg Val Leu Asp Leu
        35                  40                  45

Ser Asp Ser Cys Val Lys Asp Leu Ser Asp Ser Ile Gly Lys Leu Leu
    50                  55                  60

His Leu Arg Tyr Leu Asn Leu Ser Ser Asn Ile Lys Leu Glu Ile Ile
65                  70                  75                  80

Pro Asp Ala Ile Thr Arg Leu His Asn Leu Gln Thr Leu Leu Leu Glu
                85                  90                  95

Asp Cys Arg Ser Leu Lys Glu Leu Pro Lys Asp Phe Cys Lys Leu Val
            100                 105                 110

Lys Leu Arg His Leu Glu Leu Gln Gly Cys His Asp Leu Ile Gly Met
        115                 120                 125

Ser Phe Gly Met Asp Lys Leu Thr Ser Leu Arg Ile Leu Pro Asn Ile
    130                 135                 140

Val Val Gly Arg Lys Glu Gln Ser Val Asp Asp Glu Leu Lys Ala Leu
145                 150                 155                 160

Lys Gly Leu Thr Glu Ile Lys Gly Ser Ile Asp Ile Thr Ile Tyr Ser
```

```
                165                 170                 175
Lys Tyr Arg Arg Val Glu Gly Met Asn Gly Thr Gly Gly Ala Gly
            180                 185                 190

Tyr Leu Lys Ser Met Lys His Leu Thr Gly Val Asn Ile Thr Phe Asp
            195                 200                 205

Glu Gly Gly Cys Val Asn Pro Glu Ala Val Tyr Leu Lys Ser Met Lys
        210                 215                 220

His Leu Thr Arg Val Ile Ile Ile Phe Asp Tyr Lys Gly Gly Cys Val
225                 230                 235                 240

Asn Pro Glu Ala Val Leu Ala Thr Leu Glu Pro Pro Ser Asn Ile Lys
                245                 250                 255

Arg Leu Glu Met Trp His Tyr Ser Gly Thr Thr Ile Pro Val Trp Gly
            260                 265                 270

Arg Ala Glu Ile Asn Trp Ala Ile Ser Leu Ser His Leu Val Asp Ile
            275                 280                 285

Thr Leu Glu Asp Cys Tyr Asn Leu Gln Glu Met Pro Val Leu Ser Lys
        290                 295                 300

Leu Pro His Leu Lys Ser Leu Glu Leu Thr Glu Leu Asp Asn Leu Glu
305                 310                 315                 320

Tyr Met Glu Ser Arg Ser Ser Ser Ser Ser Asp Thr Glu Ala Ala
                325                 330                 335

Thr Pro Glu Leu Pro Thr Phe Phe Pro Ser Leu Glu Lys Leu Thr Leu
            340                 345                 350

Trp Arg Leu Asp Lys Leu Lys Gly Phe Gly Asn Arg Arg Ser Ser Ser
        355                 360                 365

Phe Pro Arg Leu Ser Lys Leu Glu Ile Trp Lys Cys Pro Asp Leu Thr
370                 375                 380

Ser Phe Pro Ser Cys Pro Ser Leu Glu Glu Leu Glu Leu Lys Glu Asn
385                 390                 395                 400

Asn Glu Ala Leu Gln Ile Ile Val Lys Ile Thr Thr Thr Arg Gly Lys
                405                 410                 415

Glu Glu Lys Glu Glu Asp Lys Asn Ala Gly Val Gly Asn Ser Gln Asp
            420                 425                 430

Asp Asp Asn Val Lys Leu Trp Lys Val Glu Ile Asp Asn Leu Gly Tyr
        435                 440                 445

Leu Lys Ser Leu Pro Thr Asn Cys Leu Thr His Leu Asp Leu Thr Ile
450                 455                 460

Ser Asp Ser Lys Glu Gly Glu Gly Glu Trp Glu Val Gly Asp Ala Phe
465                 470                 475                 480

Gln Lys Cys Val Ser Ser Leu Arg Ser Leu Thr Ile Ile Gly Asn His
                485                 490                 495

Gly Ile Asn Lys Val Lys Arg Leu Ser Gly Arg Thr Gly Leu Glu His
            500                 505                 510

Phe Thr Leu Leu Glu Ser Leu Lys Leu Ser Asp Ile Glu Asp Gln Glu
        515                 520                 525

Asp Glu Gly Glu
        530

<210> SEQ ID NO 13
<211> LENGTH: 9
<212> TYPE: PRT
<213> ORGANISM: Spinacia oleracea
<220> FEATURE:
<223> OTHER INFORMATION: motif
```

```
<400> SEQUENCE: 13

Met Ala Glu Ile Gly Tyr Ser Val Cys
1               5

<210> SEQ ID NO 14
<211> LENGTH: 6
<212> TYPE: PRT
<213> ORGANISM: Spinacia oleracea
<220> FEATURE:
<223> OTHER INFORMATION: motif

<400> SEQUENCE: 14

Lys Trp Met Cys Leu Arg
1               5

<210> SEQ ID NO 15
<211> LENGTH: 8
<212> TYPE: PRT
<213> ORGANISM: Spinacia oleracea
<220> FEATURE:
<223> OTHER INFORMATION: motif

<400> SEQUENCE: 15

His Val Gly Cys Val Val Asp Arg
1               5

<210> SEQ ID NO 16
<211> LENGTH: 9
<212> TYPE: PRT
<213> ORGANISM: Spinacia oleracea
<220> FEATURE:
<223> OTHER INFORMATION: motif

<400> SEQUENCE: 16

Asp Gln Glu Asp Glu Gly Glu Asp Asn
1               5

<210> SEQ ID NO 17
<211> LENGTH: 30
<212> TYPE: DNA
<213> ORGANISM: Spinacia oleracea
<220> FEATURE:
<223> OTHER INFORMATION: standard amplification sequence

<400> SEQUENCE: 17
gcagtcgaac atgtagctga ctcaggtcac                                    30

<210> SEQ ID NO 18
<211> LENGTH: 30
<212> TYPE: DNA
<213> ORGANISM: Spinacia oleracea
<220> FEATURE:
<223> OTHER INFORMATION: standard amplification sequence

<400> SEQUENCE: 18
tggatcactt gtgcaagcat cacatcgtag                                    30
```

PERONOSPORA RESISTANCE IN SPINACIA OLERACEA

RELATED APPLICATIONS AND INCORPORATION BY REFERENCE

This application is a continuation-in-part application of international patent application Serial No. PCT/EP2017/074807 filed 29 Sep. 2017, which published as PCT Publication No. WO 2018/060442 on 5 Apr. 2018, which claims benefit of international patent application Serial No. PCT/EP2016/001624 filed 30 Sep. 2016.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy, is named Y795400420.txt and is 59 bytes in size

FIELD OF THE INVENTION

The invention relates to an allele capable of conferring resistance to a spinach plant against multiple *Peronospora farinosa* f sp. *spinaciae* races. The invention also relates to a spinach plant, to propagation material of said spinach plant, to a cell of said spinach plant, and to seed of said spinach plant carrying the allele. The invention further relates to a method of producing a spinach plant carrying the allele and to the use of the allele in breeding to confer resistance against *Peronospora farinosa* f sp. *Spinaciae*.

BACKGROUND OF THE INVENTION

Downy mildew (*Peronospora farinosa* f. sp. *spinaciae*) is a major threat for spinach growers because it directly affects the harvested leaves. In spinach, downy mildew is caused by the oomycete *Peronospora farinosa* f. sp. *spinaciae* (formerly known as *P. effusa*). Infection makes the leaves unsuitable for sale and consumption, as it manifests itself phenotypically as yellow lesions on the older leaves, and on the abaxial leaf surface a greyish fungal growth can be observed. The infection can spread very rapidly, and it can occur both in glasshouse cultivation and in soil cultivation. The optimal temperature for formation and germination of *P. farinosa* f sp. *spinaciae* spores is 9 to 12° C., and it is facilitated by a high relative humidity. When spores are deposited on a humid leaf surface they can readily germinate and infect the leaf. Fungal growth is optimal between 8 and 20° C. and a relative humidity of >80%, and within 6 and 13 days after infection mycelium growth can be observed. Oospores of *P. farinosa* can survive in the soil for up to 3 years, or as mycelium in seeds or living plants.

To date 16 pathogenic races of spinach downy mildew (Pfs) have been officially identified and characterized, and many new candidates are observed in the field. The 16 officially recognised races of *Peronospora farinosa* f sp. *spinaciae*, are designated Pfs:1 to Pfs:16 (Irish et al. Phtypathol. Vol. 98 pg. 894-900, 2008; Plantum NL (Dutch association for breeding, tissue culture, production and trade of seed and young plants) press release, "Benoeming van Pfs: 14, een nieuwe fysio van valse meeldauw in spinazie", Sep. 19, 2012; Report Jim Correl (Univ. Arkansas) and Steven Koike (UC Cooperative Extension, Monterey County), "Race Pfs: 14—Another new race of the spinach downy mildew pathogen", Sep. 18, 2012; Plantum NL press release, "Denomination of Pfs: 15, a new race of downy mildew in spinach", Sep. 2, 2014, Plantum NL press release, "Denomination of Pfs: 16, a new race of downy mildew in spinach, Mar. 15, 2016). Races 4 to 15 were identified between 1990 and 2014, while only recently another new *Peronospora* isolate has been identified, termed UA201519B, which subsequently has been officially named Pfs:16 by the International Working Group on *Peronospora* (IWGP) (Plantum NL (Dutch association for breeding, tissue culture, production and trade of seed and young plants) press release, "Denomination of Pfs: 16, a new race of downy mildew in spinach", Mar. 15, 2016. All 16 officially recognized Pfs races are publicly available from the Department of Plant Pathology, University of Arkansas, Fayetteville, Ark. 72701, USA, and also from NAK Tuinbouw, Sotaweg 22, 2371 GD Roelofarendsveen, the Netherlands.

Especially the latest identified *Peronospora* races can break the resistance of many spinach varieties that are currently used commercially worldwide, and they thus pose a serious threat to the productivity of the spinach industry. Therefore, it is crucial to stay at the forefront of developments in this field, as *Peronospora* continuously develops the ability to break the resistances that are present in commercial spinach varieties. For this reason new resistance genes against downy mildew are very valuable assets, and they form an important research focus in breeding and particular in spinach and lettuce breeding. One of the main goals of spinach breeders is to rapidly develop spinach varieties with a resistance to as many *Peronospora* races as possible, including the latest identified races, before these races become wide-spread and pose a threat to the industry.

In commercial spinach varieties resistance against downy mildew is usually caused by so-called R-genes. R-gene mediated resistance is based on the ability of a plant to recognize the invading pathogen. In many cases this recognition occurs after the pathogen has established the first phases of interaction and transferred a so called pathogenicity (or avirulence) factor into the plant cell. These pathogenicity factors interact with host components in order to establish conditions which are favorable for the pathogen to invade the host and thereby cause disease. When a plant is able to recognize the events triggered by the pathogenicity factors a resistance response can be initiated. In many different plant pathogen interaction systems such as the interaction of spinach with different downy mildew strains, the plant initiates these events only after specific recognition of the invading pathogen.

Co-evolution of plant and pathogen has led to an arms race in which a R-gene mediated resistance is sometimes overcome as a consequence of the capability of the pathogen to interact with and modify alternative host targets or the same targets in a different way, such that the recognition is lost and infection can be established successfully resulting in disease. In order to re-establish resistance in a plant, a new R-gene has to be introduced which is able to recognize the mode of action of an alternative pathogenicity factor.

Despite the fact that the durability of R-genes is relatively low, R-genes are in spinach still the predominant form of defense against downy mildew. This is mainly due to the fact that it is the only form of defense that gives absolute resistance. So far plant breeders have been very successful in generating downy mildew resistant spinach varieties by making use of resistance genes residing in the wild germplasm of the crop species. Even though R-genes are extensively used in spinach breeding, until now not much is known of these R-genes. The R-genes present in the current commercial spinach varieties have never been characterized at the molecular level, i.e. their sequence until now was unknown. Also up until now there are no closely linked molecular markers known in the art that separate these R-genes, nor are the molecular characteristics of the genes themselves known in the art. Therefore, the search for new R-genes and R-gene identification is currently based on phenotypic assays in which many accessions are screened for possible variation in their resistance pattern. Subsequently it has to be determined through crossing and selection whether a newly observed resistance is in fact caused by an R-gene.

Citation or identification of any document in this application is not an admission that such document is available as prior art to the present invention.

SUMMARY OF THE INVENTION

Adequately responding to newly emerging downy mildew races is crucial for developing commercially successful spinach varieties. Therefore, it is the object of the invention to provide a new resistance allele conferring resistance to a newly emerged downy mildew isolate and to provide molecular biological tools for identifying this new resistance allele.

In the research leading to the present invention, it was found that different resistance genes that confer resistance to *Peronospora farinosa* f. sp. *spinaciae* in spinach are not separate resistance loci, as had been previously assumed, but that they are different alleles of the same one or two genes. These one or two genes, which are either "alpha-WOLF" type or "beta-WOLF" type genes (together referred to as "the WOLF genes") each encode a protein that belongs to the CC-NBS-LRR family (Coiled Coil-Nucleotide Binding Site-Leucine-Rich Repeat). Depending on the allelic variant (or the allelic variants) that is (are) present in a spinach plant, said plant will produce a variant of the WOLF protein that confers a certain resistance profile to pathogenic races of *Peronospora farinosa* f. sp. *spinaciae*. The research leading to the present invention has furthermore elucidated the relationship between the different alleles present in the genome of a spinach plant and the resistance profile of said plant to a number of different pathogenic races of *Peronospora farinosa* f. sp. *spinaciae*.

In the context of this invention the term "allele" or "allelic variant" is used to designate a version of the gene that is linked to a specific phenotype, i.e. resistance profile. It was found that a spinach plant may carry one or two WOLF genes. Each of these two WOLF genes encompasses multiple alleles, each allele conferring a particular resistance profile. The beta WOLF gene is located on scaffold12735 (sequence: GenBank: KQ143339.1), at position 213573-221884. In case the spinach plant also carries or only carries the alpha-WOLF gene, the alpha-WOLF gene is located at approximately the same location as where the beta-WOLF gene is located on scaffold12735 in the Viroflay genome assembly.

A screen for novel WOLF-alleles in the spinach germplasm identified a new allele of the alpha-WOLF gene conferring a new and unique resistance profile against several downy mildew races including the recently identified race pfs:16.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of a plant comprising the alpha-WOLF 15 allele of the invention in its genome were deposited with NCIMB Ltd, Ferguson Building, Craibstone Estate, Bucksburn, Aberdeen AB21 9YA, UK, on Oct. 15, 2015, under deposit accession number 42466.

The Deposit with NCIMB Ltd, under deposit accession number 42466 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

A genome assembly for spinach variety Viroflay—which is susceptible to all known pathogenic races of *Peronospora* farinosa f sp. spinaciae—is publicly available (Spinacia oleracea cultivar SynViroflay, whole genome shotgun sequencing project; Bioproject: PRJNA41497; GenBank: AYZV00000000.2; BioSample: SAMN02182572, see also Dohm et al, 2014, Nature 505: 546-549). In this genome assembly for Viroflay, the beta-WOLF gene is located on scaffold12735 (sequence: GenBank: KQ143339.1), at position 213573-221884. The sequence covered by this interval comprises the entire genomic sequence of the beta-WOLF gene of Viroflay, plus 2000 basepairs sequence upstream from the gene, plus the sequence downstream from the gene, up to the locus of the neighbouring gene that is situated downstream from the WOLF gene. Spinach variety Viroflay only possesses a single WOLF gene, namely a beta-WOLF gene, but most other spinach lines harbor a single alpha-type WOLF gene at the same location in the genome. Other spinach lines harbor two WOLF genes at approximately the same location in the genome. In such cases, the two WOLF genes are positioned adjacent to each other. In most spinach lines that harbor two WOLF genes, one of said WOLF genes belongs to the alpha-type, and the other WOLF gene belongs to the beta-type. In the research leading to the present invention, it was observed that this allelic variation in the WOLF locus is responsible for differences in resistance to pathogenic races of Peronospora farinosa f. sp. spinaciae.

The difference between an allele of an alpha-WOLF gene and an allele of a beta-WOLF gene lies in the presence of specific conserved amino acid motifs in the encoded protein sequence. As mentioned above, all WOLF proteins possess—from N- to C-terminus—the following domains that are generally known in the art: a coiled coil domain (RX-CC-like, cd14798), an NBS domain (also referred to as "NB-ARC domain", pfam00931; van der Biezen & Jones, 1998, Curr. Biol. 8: R226-R228), and leucine-rich repeats (IPRO32675) which encompass the LRR domain. In addition, all WOLF proteins comprise in their amino acid sequence the motif "MAEIGYSVC" (SEQ ID NO: 13) at the N-terminus. In addition to this, all alpha-WOLF proteins comprise the motif "KWMCLR" (SEQ ID NO: 14) in their amino acid sequence, whereas all beta-WOLF proteins comprise the motif "HVGCVVDR" (SEQ ID NO: 15) in their amino acid sequence.

The present invention relates to a new Peronospora farinosa f sp. spinaciae resistance conferring allele of the alpha-WOLF gene designated alpha-WOLF 15.

In particular, the invention relates to a Peronospora farinosa f. sp. spinaciae resistance conferring allele designated alpha-WOLF 15 wherein the protein encoded by said allele is a CC-NBS-LRR protein that comprises in its amino acid sequence: a) the motif "MAEIGYSVC" (SEQ ID NO: 13) at its N-terminus; and b) the motif "KWMCLR" (SEQ ID NO: 14); and wherein the LRR domain of the protein has in order of increased preference at least 92%, 93%, 94%, 95%, 96%, 97%, 98%, 99%, 100% sequence similarity to (SEQ ID NO: 10). Optionally, the alpha-WOLF 15 allele further comprise an additional motif in their amino acid sequence, namely "DQEDEGEDN" (SEQ ID NO: 16).

For the purpose of this invention, the LRR domain of the protein of the alpha-WOLF 15 allele is defined as the amino acid sequence that in order of increased preference has at least 92%, 93%, 94%, 95%, 96%, 97%, 98%, 99%, 100% sequence similarity to (SEQ ID NO: 10).

The skilled person is familiar with methods for the calculation of sequence similarity. Suitably sequence similarity is calculated using EMBOSS stretcher 6.6.0, using the EBLOSUM62 matrix and the resulting "similarity score The LRR domain of the alpha-WOLF 15 allele as defined herein can be determined by amplifying and sequencing the genomic DNA encoding for the amino acid sequence of LRR domain using specific primers, and subsequently translating the DNA sequence into an amino acid sequence, thereby applying common sense in choosing the correct reading frame. The skilled person is capable of doing this, using freely available online bioinformatics tools such as can be found here: expasy.org/translate/

The genomic sequence of a LRR domain of an alpha-WOLF gene such as alpha-WOLF 15 can be amplified using a primer pair having a forward primer which is a nucleic acid molecule having the sequence of (SEQ ID NO: 6) and a reverse primer which is a nucleic acid molecule having the sequence of (SEQ ID NO: 7).

PCR conditions for amplifying the LRR domain-encoding region of an alpha-WOLF gene using primers having (SEQ ID NO: 6) and (SEQ ID NO: 7) are, using Platinum Taq enzyme (Thermo Fisher Scientific): 3 minutes at 95° C. (initial denaturing step); 40 amplification cycles, each cycle consisting of: 30 seconds denaturation at 95° C., 30 seconds annealing at 60° C., and 30 seconds extension at 72° C.; 2 minutes at 72° C. (final extension step).

The LRR domain of a beta-WOLF gene, e.g. the null allele as present in variety Viroflay, can be amplified using a forward primer which is a nucleic acid molecule having the sequence of (SEQ ID NO: 8) and a reverse primer which is a nucleic acid molecule having the sequence of (SEQ ID NO: 7).

PCR conditions for amplifying the LRR domain-encoding region of a beta-WOLF gene using primers having (SEQ ID NO: 7) and (SEQ ID NO: 8) are as follows, using Platinum Taq enzyme (Thermo Fisher Scientific):—3 minutes at 95° C. (initial denaturing step); 40 amplification cycles, each cycle consisting of: 30 seconds denaturation at 95° C., 50 seconds annealing at 58° C. and 50 seconds extension at 72° C.; 2 minutes at 72° C. (final extension step).

Therefore, the invention also relates to a primer pair for amplifying the LRR domain of an alpha-WOLF gene, more in particular for amplifying the LRR domain of an alpha-WOLF 15 allele wherein the forward primer is a nucleic acid molecule having the sequence of (SEQ ID NO: 6) and the reverse primer which is a nucleic acid molecule having the sequence of (SEQ ID NO: 7). The primers disclosed herein have been specifically designed for selectively amplifying part of a WOLF gene, and not of any other CC-NBS-LRR protein-encoding genes.

The invention relates to an alpha-WOLF 15 allele which has a genomic sequence that in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to (SEQ ID NO: 1).

The invention relates to two different splice variants. In one embodiment, the invention relates to an alpha-WOLF 15 allele which has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to (SEQ ID NO: 2). This is the first splice variant of the alpha-WOLF 15 allele.

In a further embodiment the alpha-WOLF 15 allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to (SEQ ID NO: 3). This is the second splice variant.

In a further aspect of the invention the alpha-WOLF 15 allele encodes for a protein having an amino acid sequence which in order of increased preference has at least 92%, 93%, 94%, 95%, 96%, 97%, 98%, 99%, 100% sequence similarity to (SEQ ID NO: 4).

In another embodiment the alpha-WOLF 15 allele encodes for a protein having an amino acid sequence which in order of increased preference has at least 92%, 93%, 94%, 95%, 96%, 97%, 98%, 99%, 100% sequence similarity to (SEQ ID NO: 5) (isoform 1).

The alpha-WOLF 15 allele when homozygously present in a spinach plant confers complete resistance to the officially recognized *Peronospora farinosa* f Sp. *spinacea* races pfs:1, pfs:2, pfs:3, pfs:4, pfs:5, pfs:6, pfs:8, pfs:9, pfs:11, pfs:12, pfs:13, pfs:14, pfs:15, pfs:16, UA1014 and US1508 and confers intermediate resistance to pfs:10 and does not confer resistance to downy mildew race pfs:7 (See Table 1). As indicated in Table 1, a spinach plant heterozygous for the alpha-WOLF 15 allele and not carrying any other resistance conferring allele will be intermediately resistant for downy mildew races Pfs:8, and Pfs:10 and susceptible to Pfs:7.

The resistance of a spinach plant against one or more races of *Peronospora farinosa* f. sp. *spinaciae* can be determined using a seedling test. Herein, a seedling test is defined as a test wherein spinach plants are planted in trays containing growth medium, optionally fertilized twice a week after seedling emergence. Plants were inoculated at the first true leaf stage with a sporangial suspension having a concentration of approximately $2.5 \times 10^5$/ml of one of the pathogenic races of *Peronospora farinosa* f. sp. *spinaciae* or isolates to be tested. The inoculated plants are placed in a dew chamber at 18° C. with 100% relative humidity for a 24 h period, and then moved to a growth chamber at 18° C. with a 12 h photoperiod for 6 days. After 6 days, the plants are returned to the dew chamber for 24 h to induce sporulation, and subsequently scored for a disease reaction. Preferably, 30 plants per race are tested.

As used herein, a plant is completely resistant against a *Peronospora farinosa* f sp. *spinaciae* race when a plant shows no symptoms in the seedling test described herein.

As used herein, a plant is intermediately resistant against a *Peronospora farinosa* f. sp. *spinaciae* race when a plant shows only symptoms of chlorosis, or sporulation occurring only on the tips of the cotyledons in the seedling test described herein.

As used herein, a plant is susceptible to an isolate of a *Peronospora farinosa* f. sp. *spinaciae* race when a plant shows more than only symptoms of chlorosis, or when sporulation occurs on area larger than only the tips of the cotyledons in the seedling test described herein.

Another aspect of the invention relates to a spinach plant, which may comprise the alpha-WOLF 15 allele of invention, of which a representative sample of seed was deposited with the NCIMB under NCIMB accession number 42466.

In a further embodiment the plant of the invention which may comprise the alpha-WOLF 15 allele is an agronomically elite spinach plant.

In the context of this invention an agronomically elite spinach plant is a plant having a genotype that results into an accumulation of distinguishable and desirable agronomic traits which allow a producer to harvest a product of commercial significance, preferably the agronomically elite spinach plant which may comprise the alpha-WOLF 15 allele is a plant of an inbred line or a hybrid.

As used herein, a plant of an inbred line is a plant of a population of plants that is the result of three or more rounds of selfing, or backcrossing; or which plant is a double haploid. An inbred line may e.g. be a parent line used for the production of a commercial hybrid.

As used herein, a hybrid plant is a plant which is the result of a cross between two different plants having different genotypes. More in particular, a hybrid plant is the result of a cross between plants of two different inbred lines, such a hybrid plant may e.g. be a plant of an $F_1$ hybrid variety.

A plant carrying the alpha-WOLF 15 allele in heterozygous form may further comprise a beta-WOLF 0 allele as e.g. present in variety Viroflay wherein the beta-WOLF 0 allele does not confer any resistance to downy mildew. However, a plant heterozygous for the alpha-WOLF 15 allele may further comprise an allele of the alpha/beta-WOLF gene that does provide resistance to downy mildew. Preferably, such an allele would complement the alpha-WOLF 15 allele such that the spinach plant will be at least intermediately resistant to one or more other races to which the alpha-WOLF 15 allele does not provide resistance. Most preferably, the other allele of the alpha/beta-WOLF gene complements the alpha-WOLF 15 allele such that the plant is resistant to *Peronospora farinosa* f. sp. *spinaciae* races Pfs:1 to Pfs:16. In one embodiment such a plant is an agronomically elite plant.

Alternatively, the resistance profile of a plant carrying the alpha-WOLF 15 allele is complemented by a resistance conferring allele of a totally different gene. Examples of such genes are e.g. DMR1 as described in U.S. Pat. No. 8,354,570 and DMR6 as described in U.S. Pat. No. 9,121,029.

The invention thus relates to a spinach plant carrying the alpha-WOLF 15 allele and further which may comprise a genetic determinant resulting in resistance against *Peronospora farinosa* f Sp. *spinacea* races pfs:1 to pfs:16. The genetic determinant can be another resistance conferring alpha/beta-WOLF allele or a resistance conferring allele of a totally different gene.

The invention further relates to propagation material comprising the alpha-WOLF 15 allele. In one embodiment, the propagation material is suitable for sexual reproduction. Such propagation material may comprise for example a microspore, pollen, ovary, ovule, embryo sac and egg cell. In another embodiment, the propagation material is suitable for vegetative reproduction. Such propagation material may comprise for example a cutting, root, stem, cell, protoplast, and a tissue culture of regenerable cells. A part of the plant that is suitable for preparing tissue cultures is in particular a leaf, pollen, an embryo, a cotyledon, a hypocotyl, a meristematic cell, a root tip, an anther, a flower, a seed and a stem.

The invention furthermore relates to a cell of a spinach plant which may comprise the alpha-WOLF 15 allele. Such a cell may be either in isolated form or may be part of the complete plant or parts thereof and then still constitutes a cell of the invention because such a cell harbors the alpha-WOLF 15 allele that confers resistance to downy mildew. Each cell of a plant of the invention carries the genetic information that confers resistance to *Peronospora farinosa* f. sp. *spinaciae*. Such a cell of the invention may also be a regenerable cell that can be used to regenerate a new plant which may comprise the allele of the invention.

Yet another aspect of the invention relates to a method for making a hybrid spinach seed which may comprise crossing a first parent spinach plant with a second parent spinach plant and harvesting the resultant hybrid spinach seed, wherein said first and/or second parent spinach plant may comprise the alpha-WOLF 15 allele. In particular embodiment, the first and/or second parent plant is a plant of an inbred line as defined herein.

The invention further relates hybrid spinach plant grown from seed produced by crossing a first parent spinach plant with a second parent spinach plant and harvesting the resultant hybrid spinach seed, wherein said first and/or second parent spinach plant may comprise the alpha-WOLF 15 allele.

Another aspect of the invention relates to a method for identifying or selecting a spinach plant carrying the alpha-WOLF 15 allele, which may comprise determining the presence of a genomic nucleotide sequence or a part thereof in the genome of a plant, wherein said sequence has in order of increased preference 92%, 93%, 94%, 95%, 96%, 97%, 98%, 99%, 100% sequence similarity to (SEQ ID NO: 1).

The invention further relates to a method for identifying or selecting a spinach plant carrying the alpha-WOLF 15 allele, which may comprise determining the presence of a coding sequence or a part thereof in the genome of a plant, wherein said sequence has in order of increased preference 92%, 93%, 94%, 95%, 96%, 97%, 98%, 99%, 100% sequence similarity to (SEQ ID NO: 2).

The invention further relates to a method for identifying or selecting a spinach plant carrying the alpha-WOLF 15 allele, which may comprise determining the presence of a coding sequence or a part thereof in the genome of a plant, wherein said sequence has in order of increased preference 92%, 93%, 94%, 95%, 96%, 97%, 98%, 99%, 100% sequence similarity to (SEQ ID NO: 3).

Determining the genomic DNA or coding DNA sequence of at least part of a WOLF gene in the genome of a spinach plant may be performed using any suitable molecular biological method known in the art, including but not limited to (genomic) PCR amplification followed by Sanger sequencing, whole-genome-sequencing, transcriptome sequencing, sequence-specific target capture followed by next-generation sequencing (using, for example, the xGen target capture system of Integrated DNA Technologies), specific amplification of LRR-domain-which may comprise gene sequences (using, for example, the RenSeq methodology, as described in U.S. patent application Ser. No. 14/627,116, and in Jupe et al., 2013, Plant J. 76: 530-544) followed by sequencing, etcetera.

In another embodiment the invention relates to a method for identifying or selecting a plant carrying the alpha-WOLF 15 allele may comprise determining the DNA sequence coding for the LRR domain as defined herein.

In a further embodiment of the method the LRR domain of the alpha-WOLF 15 allele is determined by using a primer pair to amplify the genomic DNA region of the LRR domain. The forward primer is preferably a nucleic acid molecule having the sequence of (SEQ ID NO: 6) and the reverse primer is preferably a nucleic acid molecule having the sequence of (SEQ ID NO: 7).

Another aspect of the invention relates to a method for producing a spinach plant which may comprise resistance to *Peronospora farinosa* f. sp. *spinaciae* which may comprise: (a) crossing a plant which may comprise the alpha-WOLF 15 allele, with another plant; (b) optionally performing one or more rounds of selfing and/or crossing; and (c) optionally selecting after each round of selfing or crossing for a plant that may comprise the alpha-WOLF 15 allele.

Selecting a plant which may comprise the alpha-WOLF 15 allele can be done genotypically by determining the presence of the genomic DNA sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to (SEQ ID NO: 1).

In another embodiment, selecting a plant which may comprise the alpha-WOLF 15 allele can be done genotypically by determining the presence the coding sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to (SEQ ID NO: 2).

In another embodiment, selecting a plant which may comprise the alpha-WOLF 15 allele can be done genotypically by determining the presence the coding sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to (SEQ ID NO: 3).

Alternatively, the presence of the alpha-WOLF 15 allele can be determined phenotypically by assaying a plant in a disease test, for example the test as described herein, and identifying a plant carrying the alpha-WOLF 15 allele based on the resistance pattern as described herein and indicated in Table 1.

The invention further relates to the use of a spinach plant carrying the alpha-WOLF 15 allele in breeding to confer resistance against *Peronospora farinosa* f. sp. *spinaciae*.

The invention also relates to a breeding method for the development of spinach plants carrying the alpha-WOLF 15 allele of the invention wherein germplasm which may comprise said allele is used. Seed capable of growing into a plant which may comprise the allele of the invention and being representative for the germplasm was deposited with the NCIMB under deposit number NCIMB 42466.

In another aspect, the invention relates to a method for the production of a spinach plant which may comprise alpha-WOLF 15 allele, which method may comprise: (a) crossing a plant which may comprise the allele with another plant; (b) optionally selecting for plants which may comprise said allele in the F1; (c) optionally backcrossing the resulting F1 with the preferred parent and selecting for plants that have the said allele in the BC1F1; (d) optionally performing one or more additional rounds of selfing, crossing, and/or backcrossing, and subsequently selecting for a plant which may comprise the said allele or shows the resistance profile corresponding to said allele. The invention also encompasses a spinach plant produced by this method.

The invention also relates to a harvested leaf of a spinach plant of the invention, to a food product which may comprise a harvested leaf of a spinach plant of the invention, either in natural or in processed form.

Spinach leaves are sold in packaged form, including without limitation as pre-packaged spinach leaves or as processed in a salad which may comprise said leaves. Mention of such a package is e.g. made in U.S. Pat. No. 5,523,136, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the spinach plant of the invention, as well as leaves of spinach plants derived from the invention.

The invention further relates to a container which may comprise one or more plants of the invention, or one or more spinach plants derived from a plant of the invention, in a growth substrate for harvest of leaves from the plant, in a domestic environment. This way the consumer may pick very fresh leaves for use in salads, when the plant is in a ready-to-harvest condition.

The invention also relates to the use of a spinach plant, of which representative seed was deposited with the NCIMB under accession number NCIMB 42466, in the production of a spinach plant which may comprise the alpha-WOLF 15 allele.

In a further embodiment the said spinach plant is a hybrid, doubled haploid, or inbred spinach plant Another aspect of the invention is the use of a cell which may comprise the alpha-WOLF 15 allele for the production of a spinach plant showing resistance to *Peronospora farinosa* f. sp. *spinaciae*.

The invention also relates to the use of a tissue culture which may comprise the alpha-WOLF 15 allele for the production of a spinach plant showing resistance to *Peronospora farinosa* f. sp. *spinaciae*.

TABLE 1

| Resistance Information | |
|---|---|
| *Peronospora farinosa* f. sp. Spinaciae race | Resistance score |
| Pfs: 1 | – |
| Pfs: 2 | – |

TABLE 1-continued

| Resistance Information | |
|---|---|
| *Peronospora farinosa* f. sp. Spinaciae race | Resistance score |
| Pfs: 3 | – |
| Pfs: 4 | – |
| Pfs: 5 | – |
| Pfs: 6 | – |
| Pfs: 7 | + |
| Pfs: 8 | –* |
| Pfs: 9 | – |
| Pfs: 10 | (–) |
| Pfs: 11 | – |
| Pfs: 12 | – |
| Pfs: 13 | – |
| Pfs: 14 | – |
| Pfs: 15 | – |
| Pfs: 16 | + |
| UA1014 | – |
| US1508 | – |

Resistance profile conferred by the Alpha-WOLF 15 allele. A "–" means complete resistance against a particular downy mildew race; "(–)" means intermediate resistance against a particular downy mildew race; "+" means that the allele confers no resistance and would cause a plant only carrying the Alpha-WOLF 15 allele to be fully susceptible for that particular downy mildew race.

*The resistance against Pfs: 8 as conferred by the alpha WOLF 15 allele is only observed in homozygous state. A plant carrying the allele in heterozygous state and not carrying any other resistance conferring allele (i.e. carrying the beta-WOLF zero allele) would be intermediate resistant for Pfs: 8. Alpha-WOLF 15 resistance profile

TABLE 2

| Sequence Information | |
|---|---|
| SEQ ID NO: 1:<br>Genomic<br>sequence of<br>alpha-WOLF 15 | ATGGCCGAAATCGGATACTCGGTTTGTGCGAAACTCATCGAAGTG<br>ATTGGCAGTGAGCTGATCAAAGAGATTTGTGACACATGGGGTTAC<br>AAATCTCTTCTTGAGGACCTCAACAAAACTGTATTGACGGTCAGG<br>AACGTTCTCATTCAAGCCGGGGTGATGCGGGAGCTTACTAGTGAA<br>CAACAAGGTTTCATTGCAGACCTTAAAGATGTTGTTTATGATGCTG<br>ATGACTTGTTCGACAAGTTACTCACTCGTGCTGAGCGAAAACAGA<br>TTGATGGAAACGAAATCTCTGAAAAGGTACGTCGTTTCTTTTCCTC<br>TAGTAACAAGATCGGTCAAGCTTACTACATGTCTCGTAAGGTTAA<br>GGAAATTAAGAAGCAGTTGGATGAAATTGTTGATAGGCATACAAA<br>ATTTGGGTTTAGTGCCGAGTTTATACCTGTTTGTAGGGAAAGGGGG<br>AACGAGAGGGAAACACGTTCATATATAGATGTCAAGAATATTCTT<br>GGGAGGGATAAAGATAAGAATGATATCATAGATAGGTTGCTTAAT<br>CGTAATGGTAATGAAGCTTGTAGTTTCCTGACCATAGTGGGAGCG<br>GGAGGATTGGGAAAAACTGCTCTTGCACAACTTGTGTTCAATGAT<br>GAAAGGGTCAAAATTGAGTTCCATGATTTGAGGTATTGGGTTTGT<br>GTCTCTGATCAAGATGGGGGCCAATTTGATGTGAAAGAAATCCTT<br>TGTAAGATTTTAGAGGTGGTTACTAAGGAGAAAGTTGATAATAGT<br>TCCACATTGGAATTGGTACAAAGCCAATTTCAAGAGAAGTTAAGA<br>GGAAAGAAGTACTTCCTTGTTCTTGATGATGTATGGAACGAAGAT<br>CGTGAGAAGTGGCTTCCTTTGGAAGAGTTGTTAATGTTGGGTCAA<br>GGGGGAAGCAAGGTTGTAGTGACCGCACGTTCAGAGAAGACAGC<br>AAATGTCATAGGGAAAAGACATTTTTATACACTGGAATGTTTGTC<br>ACCAGATTATTCATGGAGCTTATTTGAAATGTCGGCTTTTCAGAAA<br>GGGCATGAGCAGGAAAACCATCACGAACTAGTTGATATTGGGAAA<br>AAGATTGTTGAAAAATGTTATAACAATCCACTTGCTATAACGGTG<br>GTAGGAAGTCTTCTTTATGGAGAGGAGATAAGTAAGTGGCGGTCA<br>TTTGAAATGAGTGAGTTGGCCAAAATTGGCAATGGGGATAATAAG<br>ATTTTGCCGATATTAAAGCTCAGTTACCATAATCTTATACCCTCGT<br>TGAAGAGTTGCTTCAGTTATTGTGCAGTGTTTCCCAAGGATCATGA<br>AATAAAGAAGGAGATGTTGATTGATCTTTGGATAGCACAAGGATA<br>CGTTGTGGCACTTGATGGAGGTCAAAGTATAGAAGATGCTGCCGA<br>AGAACATTTTGTAATTTTGTTACGGAGATGTTTCTTTCAAGATGTA<br>AAGAAGGATGAATATGGTGATGTTGATTCTGTTAAAATCCACGAC<br>TTGATGCACGATGTCGCCCAAGAAGTGGGGAGGGAGGAAATATGT<br>GTAGTGAATGATAATACAAAGAACTTGGGTGATAAAATCCGTCAT<br>GTACATGGTGATGTCAATAGATATGCACAAAGAGTCTCTCTGTGT<br>AGCCATAGCCATAAGATTCGTTCGTATATTGGTGGTGATTGTGAAA<br>AACGTTGTGTGGATACACTAATAGACAAGTGGATGTGTCTTAGGA<br>TGTTGGACTTGTCATGGTCGGATGTTAAAAATTTGCCTAATTCAAT |

TABLE 2-continued

| Sequence Information |
|---|
| AGGTAAATTGTTGCACTTGAGGTATCTTAACCTGTCAGATAATAGA |
| AATCTAAAGATACTTCCTGATGCAATTACAAGACTGCATAATTTGC |
| AGACACTGCTTTTAGAAGATTGCAGAAGTTTAAAGGAGTTGCCAA |
| AAGATTTTTGCAAATTGGTCAAACTGAGGCACTTGGAATTACAGG |
| GTTGTCATGATTTGATTGGTATGCCATTTGGAATGGATAAGCTAAC |
| TAGTCTTAGAATACTACCAAACATTGTGGTGGGTAGGAAGGAACA |
| AAGTGATGATGAGCTGAAAGCCCTAAAAGGCCTCACCGAGATAAA |
| AGGCTCCATTTCTATCAGAATCTATTCAAAGTATAGAATAGTTGAA |
| GGCATGAATGACACAGGAGGAGCTGCTTATTTGAAGAGCATGAAA |
| CATCTCAGGGAGATTGATATTACATTTTTGGGTGAATGTGTTGGCC |
| CTGAAGCTGTATTGGAAACCTTAGAGCCACCTTCAAATATCAAGA |
| GCTTATATATATATAATTACAGTGGTACAACAATTCCAGTATGGGG |
| AAGAGCAGAGATTAATTGGGCAATCTCCCTCTCACATCTCGTCGA |
| CATCCAGCTTAGTTGTTGTAGTAATTTGCAGGAGATGCCAGTGCTG |
| AGTAAACTGCCTCATTTGAAATCGCTGAAACTTGGATGGTTGGAT |
| AACTTAGAGTACATGGAGAGTAGCAGTAGCAGTGACACAGAAGC |
| AGCAACACCAGAATTACCAACATTCTTCCCTTCCCTTGAAAAACTT |
| ACTTTACAGCATCTGGAAAAGTTGAAGGGTTTTGGGAACAGGAGA |
| TCGAGTAGTTTTCCCCGCCTCTCTGAATTGGAAATCAAGAAATGCC |
| CAGATCTAACGTCATTTCCTTCTTGTCCAAGCCTTGAGAAGTTGGA |
| ATTGAAAGAAAGCAATGAAGCATTGCAAATAATAGTAAAAATAA |
| CAACAAGAGGTAAAGAAAAAGAAGAGAACAATAATGCTGGTGTT |
| AGAAATTCACAAGATGATGACAAAGTCAAATTACGGAAGATGGTG |
| ATAGACAATCTGGGTTATCTCACGGGGGTTGATATTAGATTTGATG |
| ATAGAGAAGGTGGATTTGTTAACCCTGAAGCTGTGTTGGCAACCC |
| TAGAGCCACCTTCAAATATCAAGAGCTTATCTATACATCGTTTTGA |
| TGGTAAAACACTTCCAGTATGGGGAAGAGCAGAGATTAATTGGGC |
| AATCTCCCTCTCACATCTTGTCGACATCCAGCTTTGGCATTGTCGT |
| AATTTGCAGGAGATGCCAGTGCTGAGTAAACTGCCTCATTTGAAA |
| TCACTGGAACTTTATAATTTGATTAGTTTAGAGTACATGGAGAGCA |
| CAAGCAGAAGCAGTAGCAGTGACACAGAAGCAGCAACACCAGA |
| TTACCAACATTCTTCCCTTCCCTTGAAAAACTTAGACTTTGGTATCT |
| GGAAAAGTTGAAGGGTTTGGGGAACAGGAGACCGAGTAGTTTTCC |
| CCGCCTCTCTGAATTGGAAATCTGGGAATGCCCAGATCTAACGTG |
| GTTTCCTCCTTGTCCAAGCCTTAAAACGTTGAAATTGGAAAAAAAC |
| AATGAAGCGTTGCAAATAATAGTAAAAATAACAACAACAAGAGG |
| TAAAGAAGAAAAAGAAGAAGACAAGAATGCTGGTGTTGGAAATT |
| CACAAGATGATGACAATGTCAAATTACGGAAGGTGGAAATAGAC |
| AATGTGAGTTATCTCAAATCACTGCCCACAAATTGTCTTACTCACC |
| TCAAAATAACTGGAATAGATTACAGGGAGGGGGAGATTGAATCA |
| GATTCCGTGGAGGAGGAGATTGAATTGGAAGTTGGGGAGGCATTT |
| CAGAAGTGTGCATCTTCTTTGAGAAGCCTCATCATAATCGGAAATC |
| ACGGAATAAATAAAGTGATGAGACTGTCTGGAAGAACAGGGTTG |
| GAGCATTTCACTCTGTTGGACTCACTCAAATTTTCAAAGATAGAAG |
| ACCAGGAAGATGAGGGCGAAGACAACATCATATTCTGGAAATCCT |
| TTCCTCAAAACCTTCGCAGTTTGAGAATTAAAGACTCTGACAAAAT |
| GACAAGTTTGCCCATGGGGATGCAGTACTTAACCTCCCTCCAAAC |
| CCTCGAACTATCATATTGTGATGAATTGAATTCCCTTCCAGAATGG |
| ATAAGCAGCTTATCATCTCTTCAATACCTGCGCATATACTACTGTC |
| CAGCCCTGAAATCACTACCAGAAGCAATGCGGAACCTCACCTCCC |
| TTCAGACACTTGGGATATCGGATTGTCCAGACCTAGTTAAAAGAT |
| GCAGAAAACCCAACGGCAAGGACTATCCCAAAATTCAACACATCC |
| CCAAAATTGTAAGTCATTGCAGAAAGTAATTTATTCATTTATATTT |
| ATTTTATGCTTAGAATGATATACGCAGTCGTCCTTTGGTTTCAAAT |
| CTTGAATTTGGTTTTTGTTTTCTTTCTTTGTTTCTTTATTCAACACCA |
| GCCCATTTATGATTGATTCATTAAAAAAAGGATGGAGTTTTATGGA |
| TTTGAAGAAGACAACGAATTGAGATTCCTGGGGTTTTCTTTTTGTT |
| GGGGTTGGATTTCATGTATATGTTGCTGATTAAATACGAGACTGAT |
| GATGATGATGTGTTTATGGGTTTTAAATCAGATTAAATATATGGGA |
| AATGCAAGTTAATTTGGGATGCACATAAGGTGTTTGCTGAAATGT |
| CTATGAGAAATGTTGTTTCTTGGACTTAGAATGATATACACTGTCG |
| TCCTTTGGTTTCCAATCTTACATTTGGTTTGTGTTTTCTTAGTTTGTT |
| TCTTTAATCAACACCAACCCGTTTTTTTAAACTACCTGCAACTAC |
| TAATTTACGTTTACCCTGTATCTCAGGTACTAAATGAATATTGGTG |
| ATTTTCAGTTACTCAACACTAGCTTGATCCTGAACGCACCCAACCT |
| TCAGGTTAGAATCCGGCTTACTCATCCTTTTGTCCAGTTTTCAAGT |
| AATTGTTTTGGCAGGATCAATTCTCTAATTGTTGTACACCGTATAT |
| TGCAATTTATAGTGACTACAGTTAATGAATGTTTACAAAAAATTAG |
| TCATGTAAAAACTTCTTCTGTCCATTACATAAACTCTTTTTCTCT |
| TTCTAACTTATCATGTTCATGTCTAAACAATTAAACATGCTCACAT |
| CAATGTTCATTTAAGCTAACTTACTTCTGTAAGAGAGCGAGCTAGT |
| TAAAAACTCCTTTAACTTTCTGTTTTATACTCAGGACATGGATTGA |
| TGCAAGCATGAAGAACTTCGGGAATTTGCTAAAACTCTACCAAAG |
| CGATGAGAGTTTGGACTTTATTTCACTTGAAGTCAGGGACTGTCAA |
| CAAAGCCACAGTGTGCATGTTGGCTGTTTCACTTGGACGATAAAA |
| AGGTTTATTTAATTGTTTTCCTAAGTGTATTTGGCTTACAAGCTTTT |
| ACTTTTCACTTGAAAGGGTTTTTCTTGTTTTAAGCTTTTCGAATTAG |
| AGTTTTCGGTTGAAGTAAGAGTAGTCGTATTAGTCTTTTACCTAAG |

TABLE 2-continued

| | Sequence Information |
|---|---|
| | GAAGACTCTTTTTTGTAATTTTCAGACTATGCAATTCAAGTTTTCG<br>AGTGTTTTCTTGCTTGTGTGATTGTGAGTTGGTGAATTCGTCTTTCA<br>TACATTTTGAGATTATCAGAAGCTTTATGCTCCACCGGTAGTCTAG<br>TACCTTTTCTGTTACTGTGCAGGGAAGTAATCTGGTACCTTCTATA<br>TATATGGAAAAACATACATTATACATTATGCAAAATTCTTACAGGT<br>TAGTTACTTCCTGGAACTTCATTTACACTTAGTTTTTTTTGTTCCAT<br>TCCCTCGGAATCAAGTCATTCCCTCTGAGAAATATGTAATGAACTT<br>CTGTATGTTGCTGTTTGGTTCCTGTTTTAATCTTCAATTTTCTTGTA<br>TAGTTACAGCTGCATTTACAATGAAGTTTAAGCAGACACTCTCTTT<br>ATATAGTGCCTCTTTCTGGAGCACCGTAGAGCTGTCTGTGGTTGAT<br>CACCATCTGCTGCCGAGAGATTCAGCAATCGCGTGTTTGATCAGGT<br>AAAAGTTTTTATGTCAATGTGTTTTTTTTCCGTTTGATCAATTTAT<br>GTCTGTATTCAGATTCTTATCTTCTTACAGTAGCATAACACATTGTT<br>TCTTTCATTTATGTAAACTGTTTCAAGATTACAGAGATGTATGCTT<br>CAGTCGACATTGATGATAACTTAAGATGGCATTCCTACAACAGTT<br>GCAGGCGCATTCTAACTCCGGCAATTCTAGTTAGGCAAGAGGAGC<br>ATTGCCAATACCTGCCACCTCTGGGATTACTATACCAGGGTTGAA<br>GTTTATGGAAGACACCAGCTATGCACAAGCCTTCAAGGGGTCATC<br>CTACATAACAAGTTGAACCAACCAATTGCTTGTTGGTTCAGTGGTA<br>ATTGAAGCTGAATTTGGTAGGGATGGCCCGTGTTCGATCCCCACA<br>ACAACAATTGGGAGGGACTGGAACCTATCCACACAGAACTCGCC<br>CTGAATCCGGATTAGCCCTAAGGGTGAACGGGGTGCTAACACCAA<br>AAAAAAAAACATAACAAGTTGAACCAAACATACTTTGTTTGAATT<br>GAAGATTTAGTGATTTCATTTGATCGATTGAGATGTCTTATTATAA<br>GCGTATATGCTCTTGGATTTGGCCACTTAGGTGTTGTTTGACAATT<br>GGACATTAACTCGCTTTTATATTTTCTTTTCTCTTAGGAAAGGTGAT<br>CCTGAGAATTTATATTGGAACACTTTTTTTTTCTCACTAGCTTTAAA<br>AAAGTGTTCTGTGTTACCTGCAATTCAATTTGATTATTTTTCACATA<br>GTTTTACCTGAAAAAGTGTTACCTGAAAAAGTGTTACCTGAAAAT<br>CAACTGACATAAGTTTTTGTTTGGATCCAATTAAGGACACTAGATA<br>AATCGGAATAAATAATCAACCAATTAAGTACTTCATAATTAAATA<br>TGAAGTGTATTATTATCTTATGCTTGTGACATTGAAGGATGTTATG<br>ATATTTTAACTCAATACCTTGCAAAATATACTGGTTAAATTTCTTA<br>ACAAGGTAACTTGGCAACA |
| (SEQ ID NO: 2):<br>cds alpha-WOLF<br>15 | ATGGCCGAAATCGGATACTCGGTTTGTGCGAAACTCATCGAAGTG<br>ATTGGCAGTGAGCTGATCAAAGAGATTTGTGACACATGGGGTTAC<br>AAATCTCTTCTTGAGGACCTCAACAAAACTGTATTGACGGTCAGG<br>AACGTTCTCATTCAAGCCGGGGTGATGCGGGAGCTTACTAGTGAA<br>CAACAAGGTTTCATTGCAGACCTTAAAGATGTTGTTTATGATGCTG<br>ATGACTTGTTCGACAAGTTACTCACTCGTGCTGAGCGAAAACAGA<br>TTGATGGAAACGAAATCTCTGAAAAGGTACGTCGTTTCTTTTCCTC<br>TAGTAACAAGATCGGTCAAGCTTACTACATGTCTCGTAAGGTTAA<br>GGAAATTAAGAAGCAGTTGGATGAAATTGTTGATAGGCATACAAA<br>ATTTGGGTTTAGTGCCGAGTTTATACCTGTTTGTAGGGAAAGGGGG<br>AACGAGAGGGAAACACGTTCATATATAGATGTCAAGAATATTCTT<br>GGGAGGGATAAAGATAAGAATGATATCATAGATAGGTTGCTTAAT<br>CGTAATGGTAATGAAGCTTGTAGTTTCCTGACCATAGTGGGAGCG<br>GGAGGATTGGGAAAAACTGCTCTTGCACAACTTGTGTTCAATGAT<br>GAAAGGGTCAAAATTGAGTTCCATGATTTGAGGTATTGGGTTTGT<br>GTCTCTGATCAAGATGGGGCCAATTTGATGTGAAAGAAATCCTT<br>TGTAAGATTTTAGAGGTGGTTACTAAGGAGAAAGTTGATAATAGT<br>TCCACATTGGAATTGGTACAAAGCCAATTTCAAGAGAAGTTAAGA<br>GGAAAGAAGTACTTCCTTGTTCTTGATGATGTATGGAACGAAGAT<br>CGTGAGAAGTGGCTTCCTTTGGAAGAGTTGTTAATGTTGGGTCAA<br>GGGGGAAGCAAGGTTGTAGTGACCGCACGTTCAGAGAAGACAGC<br>AAATGTCATAGGGAAAAGACATTTTTATACACTGGAATGTTTGTC<br>ACCAGATTATTCATGGAGCTTATTTGAAATGTCGGCTTTTCAGAAA<br>GGGCATGAGCAGGAAAACCATCACGAACTAGTTGATATTGGGAAA<br>AAGATTGTTGAAAAATGTTATAACAATCCACTTGCTATAACGGTG<br>GTAGGAAGTCTTCTTTATGGAGAGGAGATAAGTAAGTGGCGGTCA<br>TTTGAAATGAGTGAGTTGGCCAAAATTGGCAATGGGGATAATAAG<br>ATTTTGCCGATATTAAAGCTCAGTTACCATAATCTTATACCCTCGT<br>TGAAGAGTTGCTTCAGTTATTGTGCAGTGTTTCCCAAGGATCATGA<br>AATAAAGAAGGAGATGTTGATTGATCTTTGGATAGCACAAGGATA<br>CGTTGTGGCACTTGATGGAGGTCAAAGTATAGAAGATGCTGCCGA<br>AGAACATTTTGTAATTTTGTTACGGAGATGTTTCTTTCAAGATGTA<br>AAGAAGGATGAATATGGTGATGTTGATTCTGTTAAAATCCACGAC<br>TTGATGCACGATGTCGCCCAAGAAGTGGGGAGGGAGGAAATATGT<br>GTAGTGAATGATAATACAAAGAACTTGGGTGATAAAATCCGTCAT<br>GTACATGGTGATGTCAATAGATATGCACAAAGAGTCTCTCTGTGT<br>AGCCATAGCCATAAGATTCGTTCGTATATTGGTGGTGATTGTGAAA<br>AACGTTGTGTGGATACACTAATAGACAAGTGGATGTGTCTTAGGA<br>TGTTGGACTTGTCATGGTCGGATGTTAAAAATTTGCCTAATTCAAT<br>AGGTAAATTGTTGCACTTGAGGTATCTTAACCTGTCAGATAATAGA<br>AATCTAAAGATACTTCCTGATGCAATTACAAGACTGCATAATTTGC<br>AGACACTGCTTTTAGAAGATTGCAGAAGTTTAAAGGAGTTGCCAA<br>AAGATTTTTGCAAATTGGTCAAACTGAGGCACTTGGAATTACAGG |

TABLE 2-continued

| | Sequence Information |
|---|---|
| | GTTGTCATGATTTGATTGGTATGCCATTTGGAATGGATAAGCTAAC |
| | TAGTCTTAGAATACTACCAAACATTGTGGTGGGTAGGAAGGAACA |
| | AAGTGATGATGAGCTGAAAGCCCTAAAAGGCCTCACCGAGATAAA |
| | AGGCTCCATTTCTATCAGAATCTATTCAAAGTATAGAATAGTTGAA |
| | GGCATGAATGACACAGGAGGAGCTGCTTATTTGAAGAGCATGAAA |
| | CATCTCAGGGAGATTGATATTACATTTTTGGGTGAATGTGTTGGCC |
| | CTGAAGCTGTATTGGAAACCTTAGAGCCACCTTCAAATATCAAGA |
| | GCTTATATATATAATTACAGTGGTACAACAATTCCAGTATGGGG |
| | AAGAGCAGAGATTAATTGGGCAATCTCCCTCTCACATCTCGTCGA |
| | CATCCAGCTTAGTTGTTGTAGTAATTTGCAGGAGATGCCAGTGCTG |
| | AGTAAACTGCCTCATTTGAAATCGCTGAAACTTGGATGGTTGGAT |
| | AACTTAGAGTACATGGAGAGTAGCAGTAGCAGTGACACAGAAGC |
| | AGCAACACCAGAATTACCAACATTCTTCCCTTCCCTTGAAAAACTT |
| | ACTTTACAGCATCTGGAAAAGTTGAAGGGTTTTGGGAACAGGAGA |
| | TCGAGTAGTTTTCCCCGCCTCTCTGAATTGGAAATCAAGAAATGCC |
| | CAGATCTAACGTCATTTCCTTCTTGTCCAAGCCTTGAGAAGTTGGA |
| | ATTGAAGAAAGCAATGAAGCATTGCAAATAATAGTAAAAATAA |
| | CAACAAGAGGTAAAGAAAAAGAAGAGAACAATAATGCTGGTGTT |
| | AGAAATTCACAAGATGATGACAAAGTCAAATTACGGAAGATGGTG |
| | ATAGACAATCTGGGTTATCTCACGGGGGTTGATATTAGATTTGATG |
| | ATAGAGAAGGTGGATTTGTTAACCCTGAAGCTGTGTTGGCAACCC |
| | TAGAGCCACCTTCAAATATCAAGAGCTTATCTATACATCGTTTTGA |
| | TGGTAAAACACTTCCAGTATGGGGAAGAGCAGAGATTAATTGGGC |
| | AATCTCCCTCTCACATCTTGTCGACATCCAGCTTTGGCATTGTCGT |
| | AATTTGCAGGAGATGCCAGTGCTGAGTAAACTGCCTCATTTGAAA |
| | TCACTGGAACTTTATAATTTGATTAGTTTAGAGTACATGGAGAGCA |
| | CAAGCAGAAGCAGTAGCAGTGACACAGAAGCAGCAACACCAGAA |
| | TTACCAACATTCTTCCCTTCCCTTGAAAAACTTAGACTTTGGTATCT |
| | GGAAAAGTTGAAGGGTTTGGGGAACAGGAGACCGAGTAGTTTTCC |
| | CCGCCTCTCTGAATTGGAAATCTGGGAATGCCCAGATCTAACGTG |
| | GTTTCCTCCTTGTCCAAGCCTTAAAACGTTGAAATTGGAAAAAAAC |
| | AATGAAGCGTTGCAAATAATAGTAAAAATAACAACAACAAGAGG |
| | TAAAGAAGAAAAAGAAGAAGACAAGAATGCTGGTGTTGGAAATT |
| | CACAAGATGATGACAATGTCAAATTACGGAAGGTGGAAATAGAC |
| | AATGTGAGTTATCTCAAATCACTGCCCACAAATTGTCTTACTCACC |
| | TCAAAATAACTGGAATAGATTACAGGGAGGGGGAGATTGAATCA |
| | GATTCCGTGGAGGAGGAGATTGAATTGGAAGTTGGGGAGGCATTT |
| | CAGAAGTGTGCATCTTCTTTGAGAAGCCTCATCATAATCGGAAATC |
| | ACGGAATAAATAAAGTGATGAGACTGTCTGGAAGAACAGGGTTG |
| | GAGCATTTCACTCTGTTGGACTCACTCAAATTTTCAAAGATAGAAG |
| | ACCAGGAAGATGAGGGCGAAGACAACATCATATTCTGGAAATCCT |
| | TTCCTCAAAACCTTCGCAGTTTGAGAATTAAAGACTCTGACAAAAT |
| | GACAAGTTTGCCCATGGGGATGCAGTACTTAACCTCCCTCCAAAC |
| | CCTCGAACTATCATATTGTGATGAATTGAATTCCCTTCCAGAATGG |
| | ATAAGCAGCTTATCATCTCTTCAATACCTGCGCATATACTACTGTC |
| | CAGCCCTGAAATCACTACCAGAAGCAATGCGGAACCTCACCTCCC |
| | TTCAGACACTTGGGATATCGGATTGTCCAGACCTAGTTAAAAGAT |
| | GCAGAGAAACCCAACGGCAAGGACTATCCCAAAATTCAACACATCC |
| | CCAAAATTGTACTAAATGAATATTGGTGA |
| (SEQ ID NO: 3): cds of alpha-WOLF 15 (isoform 1) | ATGGCCGAAATCGGATACTCGGTTTGTGCGAAACTCATCGAAGTG |
| | ATTGGCAGTGAGCTGATCAAAGAGATTTGTGACACATGGGGTTAC |
| | AAATCTCTTCTTGAGGACCTCAACAAAACTGTATTGACGGTCAGG |
| | AACGTTCTCATTCAAGCCGGGTGATGCGGGAGCTTACTAGTGAA |
| | CAACAAGGTTTCATTGCAGACCTTAAAGATGTTGTTTATGATGCTG |
| | ATGACTTGTTCGACAAGTTACTCACTCGTGCTGAGCGAAAACAGA |
| | TTGATGGAAACGAAATCTCTGAAAAGGTACGTCGTTTCTTTTCCTC |
| | TAGTAACAAGATCGGTCAAGCTTACTACATGTCTCGTAAGGTTAA |
| | GGAAATTAAGAAGCAGTTGGATGAAATTGTTGATAGGCATACAAA |
| | ATTTGGGTTTAGTGCCGAGTTTATACCTGTTTGTAGGGAAAGGGGG |
| | AACGAGAGGGAAACACGTTCATATATAGATGTCAAGAATATTCTT |
| | GGGAGGGATAAAGATAAGAATGATATCATAGATAGGTTGCTTAAT |
| | CGTAATGGTAATGAAGCTTGTAGTTTCCTGACCATAGTGGGAGCG |
| | GGAGGATTGGGAAAAACTGCTCTTGCACAACTTGTGTTCAATGAT |
| | GAAAGGGTCAAAATTGAGTTCCATGATTTGAGGTATTGGGTTTGT |
| | GTCTCTGATCAAGATGGGGCCAATTTGATGTGAAAGAAATCCTT |
| | TGTAAGATTTTAGAGGTGGTTACTAAGGAGAAAGTTGATAATAGT |
| | TCCACATTGGAATTGGTACAAAGCCAATTTCAAGAGAAGTTAAGA |
| | GGAAAGAAGTACTTCCTTGTTCTTGATGATGTATGGAACGAAGAT |
| | CGTGAGAAGTGGCTTCCTTTGGAAGAGTTGTTAATGTTGGGTCAA |
| | GGGGGAAGCAAGGTTGTAGTGACCGCACGTTCAGAGAAGACAGC |
| | AAATGTCATAGGGAAAAGACATTTTTATACACTGGAATGTTTGTC |
| | ACCAGATTATTCATGGAGCTTATTTGAAATGTCGGCTTTTCAGAA |
| | GGGCATGAGCAGGAAAACCATCACGAACTAGTTGATATTGGGAAA |
| | AAGATTGTTGAAAAATGTTATAACAATCCACTTGCTATAACGGTG |
| | GTAGGAAGTCTTCTTTATGGAGAGGAGATAAGTAAGTGGCGGTCA |
| | TTTGAAATGAGTGAGTTGGCCAAAATTGGCAATGGGATAATAAG |
| | ATTTTGCCGATATTAAAGCTCAGTTACCATAATCTTATACCCTCGT |

TABLE 2-continued

Sequence Information

|  |  |
|---|---|
|  | TGAAGAGTTGCTTCAGTTATTGTGCAGTGTTTCCCAAGGATCATGA<br>AATAAAGAAGGAGATGTTGATTGATCTTTGGATAGCACAAGGATA<br>CGTTGTGGCACTTGATGGAGGTCAAAGTATAGAAGATGCTGCCGA<br>AGAACATTTTGTAATTTTGTTACGGAGATGTTTCTTTCAAGATGTA<br>AAGAAGGATGAATATGGTGATGTTGATTCTGTTAAAATCCACGAC<br>TTGATGCACGATGTCGCCCAAGAAGTGGGGAGGGAGGAAATATGT<br>GTAGTGAATGATAATACAAAGAACTTGGGTGATAAAATCCGTCAT<br>GTACATGGTGATGTCAATAGATATGCACAAAGAGTCTCTCTGTGT<br>AGCCATAGCCATAAGATTCGTTCGTATATTGGTGGTGATTGTGAAA<br>AACGTTGTGTGGATACACTAATAGACAAGTGGATGTGTCTTAGGA<br>TGTTGGACTTGTCATGGTCGGATGTTAAAAATTTGCCTAATTCAAT<br>AGGTAAATTGTTGCACTTGAGGTATCTTAACCTGTCAGATAATAGA<br>AATCTAAAGATACTTCCTGATGCAATTACAAGACTGCATAATTTGC<br>AGACACTGCTTTTAGAAGATTGCAGAAGTTTAAAGGAGTTGCCAA<br>AAGATTTTTGCAAATTGGTCAAACTGAGGCACTTGGAATTACAGG<br>GTTGTCATGATTTGATTGGTATGCCATTTGGAATGGATAAGCTAAC<br>TAGTCTTAGAATACTACCAAACATTGTGGTGGGTAGGAAGGAACA<br>AAGTGATGATGAGCTGAAAGCCCTAAAAGGCCTCACCGAGATAAA<br>AGGCTCCATTTCTATCAGAATCTATTCAAAGTATAGAATAGTTGAA<br>GGCATGAATGACACAGGAGGAGCTGCTTATTTGAAGAGCATGAAA<br>CATCTCAGGGAGATTGATATTACATTTTTGGGTGAATGTGTTGGCC<br>CTGAAGCTGTATTGGAAACCTTAGAGCCACCTTCAAATATCAAGA<br>GCTTATATATATATATAATTACAGTGGTACAACAATTCCAGTATGGG<br>AAGAGCAGAGATTAATTGGGCAATCTCCCTCTCACATCTCGTCGA<br>CATCCAGCTTAGTTGTTGTAGTAATTTGCAGGAGATGCCAGTGCTG<br>AGTAAACTGCCTCATTTGAAATCGCTGAAACTTGGATGGTTGGAT<br>AACTTAGAGTACATGGAGAGTAGCAGTAGCAGTGACACAGAAGC<br>AGCAACACCAGAATTACCAACATTCTTCCCTTCCCTTGAAAAACTT<br>ACTTTACAGCATCTGGAAAAGTTGAAGGGTTTTGGGAACAGGAGA<br>TCGAGTAGTTTTCCCCGCCTCTCTGAATTGGAAATCAAGAAATGCC<br>CAGATCTAACGTCATTTCCTTCTTGTCCAAGCCTTGAGAAGTTGGA<br>ATTGAAAGAAAGCAATGAAGCATTGCAAATAATAGTAAAAATAA<br>CAACAAGAGGTAAAGAAAAAGAAGAGAACAATAATGCTGGTGTT<br>AGAAATTCACAAGATGATGACAAAGTCAAATTACGGAAGATGGTG<br>ATAGACAATCTGGGTTATCTCACGGGGGTTGATATTAGATTTGATG<br>ATAGAGAAGGTGGATTTGTTAACCCTGAAGCTGTGTTGGCAACCC<br>TAGAGCCACCTTCAAATATCAAGAGCTTATCTATACATCGTTTTGA<br>TGGTAAAACACTTCCAGTATGGGAAGAGCAGAGATTAATTGGGC<br>AATCTCCCTCTCACATCTTGTCGACATCCAGCTTTGGCATTGTCGT<br>AATTTGCAGGAGATGCCAGTGCTGAGTAAACTGCCTCATTTGAAA<br>TCACTGGAACTTTATAATTTGATTAGTTTAGAGTACATGGAGAGCA<br>CAAGCAGAAGCAGTAGCAGTGACACAGAAGCAGCAACACCAGAA<br>TTACCAACATTCTTCCCTTCCCTTGAAAAACTTAGACTTTGGTATCT<br>GGAAAAGTTGAAGGGTTTGGGGAACAGGAGACCGAGTAGTTTTCC<br>CCGCCTCTCTGAATTGGAAATCTGGGAATGCCCAGATCTAACGTG<br>GTTTCCTCCTTGTCCAAGCCTTAAAACGTTGAAATTGGAAAAAAC<br>AATGAAGCGTTGCAAATAATAGTAAAAATAACAACAACAAGAGG<br>TAAAGAAGAAAAAGAAGAAGACAAGAATGCTGGTGTTGGAAATT<br>CACAAGATGATGACAATGTCAAATTACGGAAGGTGGAAATAGAC<br>AATGTGAGTTATCTCAAATCACTGCCCACAAATTGTCTTACTCACC<br>TCAAAATAACTGGAATAGATTACAGGGAGGGGGAGATTGAATCA<br>GATTCCGTGGAGGAGGAGATTGAATTGGAAGTTGGGGAGGCATTT<br>CAGAAGTGTGCATCTTCTTTGAGAAGCCTCATCATAATCGGAAATC<br>ACGGAATAAATAAAGTGATGAGACTGTCTGGAAGAACAGGGTTG<br>GAGCATTTCACTCTGTTGGACTCACTCAAATTTTCAAAGATAGAAG<br>ACCAGGAAGATGAGGGCGAAGACAACATCATATTCTGGAAATCCT<br>TTCCTCAAAACCTTCGCAGTTTGAGAATTAAAGACTCTGACAAAAT<br>GACAAGTTTGCCCATGGGGATGCAGTACTTAACCTCCCTCCAAAC<br>CCTCGAACTATCATATTGTGATGAATTGAATTCCCTTCCAGAATGG<br>ATAAGCAGCTTATCATCTCTTCAATACCTGCGCATATACTACTGTC<br>CAGCCCTGAAATCACTACCAGAAGCAATGCGGAACCTCACCTCCC<br>TTCAGACACTTGGGATATCGGATTGTCCAGACCTAGTTAAAAGAT<br>GCAGAAAACCCAACGGCAAGGACTATCCCAAAATTCAACACATCC<br>CCAAAATTTTACTCAACACTAGCTTGATCCTGAACGCACCCAACCT<br>TCAGGACATGGATTGA |
| (SEQ ID NO: 4):<br>protein sequence<br>of alpha-WOLF<br>15 | MAEIGYSVCAKLIEVIGSELIKEICDTWGYKSLLEDLNKTVLTVRNVLI<br>QAGVMRELTSEQQGFIADLKDVVYDADDLFDKLLTRAERKQIDGNEI<br>SEKVRRFFSSSNKIGQAYYMSRKVKEIKKQLDEIVDRHTKFGFSAEFIP<br>VCRERGNERETRSYIDVKNILGRDKDKNDIIDRLLNRNGNEACSFLTI<br>VGAGGLGKTALAQLVFNDERVKIEFHDLRYWVCVSDQDGGQFDVK<br>EILCKILEVVTKEKVDNSSTLELVQSQFQEKLRGKKYFLVLDDWNE<br>DREKWLPLEELLMLGQGGSKVVVTARSEKTANVIGKRHFYTLECLSP<br>DYSWSLFEMSAFQKGHEQENHHELVDIGKKIVEKCYNNPLAITVVGS<br>LLYGEEISKWRSFEMSELAKIGNGDNKILPILKLSYHNLIPSLKSCFSYC<br>AVFPKDHEIKKEMLIDLWIAQGYVVALDGGQSIEDAAEEHFVILLRRC<br>FFQDVKKDEYGDVDSVKIHDLMHDVAQEVGREEICVVNDNTKNLGD<br>KIRHVHGDVNRYAQRVSLCSHSHKIRSYIGGDCEKRCVDTLIDKWMC |

TABLE 2-continued

Sequence Information

|  |  |
|---|---|
|  | LRMLDLSWSDVKNLPNSIGKLLHLRYLNLSDNRNLKILPDAITRLHNL<br>QTLLLEDCRSLKELPKDFCKLVKLRHLELQGCHDLIGMPFGMDKLTS<br>LRILPNIVVGRKEQSDDELKALKGLTEIKGSISIRIYSKYRIVEGMNDT<br>GGAAYLKSMKHLREIDITFLGECVGPEAVLETLEPPSNIKSLYIYNYSG<br>TTIPVWGRAEINWAISLSHLVDIQLSCCSNLQEMPVLSKLPHLKSLKL<br>GWLDNLEYMESSSSSDTEAATPELPTFFPSLEKLTLQHLEKLKGFGNR<br>RSSSFPPRLSELEIKKCPDLTSFPSCPSLEKLELKESNEALQIIVKITTRGK<br>EKEENNNAGVRNSQDDDKVKLRKMVIDNLGYLTGVDIRFDDREGGF<br>VNPEAVLATLEPPSNIKSLSIHRFDGKTLPVWGRAEINWAISLSHLVDI<br>QLWHCRNLQEMPVLSKLPHLKSLELYNLISLEYMESTSRSSSSDTEAA<br>TPELPTFFPSLEKLRLWYLEKLKGLGNRRPSSFPRLSELEIWECPDLTW<br>FPPCPSLKTLKLEKNNEALQIIVKITTTRGKEEKEEDKNAGVGNSQDD<br>DNVKLRKVEIDNVSYLKSLPTNCLTHLKITGIDYREGEIESDSVEEEIE<br>LEVGEAFQKCASSLRSLIIIGNHGINKVMRLSGRTGLEHFTLLDSLKFS<br>KIEDQEDEGEDNIIFWKSFPQNLRSLRIKDSDKMTSLPMGMQYLTSLQ<br>TLELSYCDELNSLPEWISSLSSLQYLRIYYCPALKSLPEAMRNLTSLQT<br>LGISDCPDLVKRCRKPNGKDYPKIQHIPKIVLNEYW* |
| (SEQ ID NO: 5):<br>protein sequence<br>of alpha-WOLF<br>15 (isoform 1) | MAEIGYSVCAKLIEVIGSELIKEICDTWGYKSLLEDLNKTVLTVRNVLI<br>QAGVMRELTSEQQGFIADLKDVVYDADDLFDKLLTRAERKQIDGNEI<br>SEKVRRFFSSSNKIGQAYYMSRKVKEIKKQLDEIVDRHTKFGFSAEFIP<br>VCRERGNERETRSYIDVKNILGRDKDKNDIIDRLLNRNGNEACSFLTI<br>VGAGGLGKTALAQLVFNDERVKIEFHDLRYWVCVSDQDGGQFDVK<br>EILCKILEVVTKEKVDNSSTLELVQSQFQEKLRGKKYFLVLDDVWNE<br>DREKWLPLEELLMLGQGGSKVVVTARSEKTANVIGKRHFYTLECLSP<br>DYSWSLFEMSAFQKGHEQENHHELVDIGKKIVEKCYNNPLAITVVGS<br>LLYGEEISKWRSFEMSELAKIGNGDNKILPILKLSYHNLIPSLKSCFSYC<br>AVFPKDHEIKKEMLIDLWIAQGYVVALDGGQSIEDAAEEHFVILLRRC<br>FFQDVKKDEYGDVDSVKIHDLMHDVAQEVGREEICVVNDNTKNLGD<br>KIRHVHGDVNRYAQRVSLCSHSHKIRSYIGGDCEKRCVDTLIDKWMC<br>LRMLDLSWSDVKNLPNSIGKLLHLRYLNLSDNRNLKILPDAITRLHNL<br>QTLLLEDCRSLKELPKDFCKLVKLRHLELQGCHDLIGMPFGMDKLTS<br>LRILPNIVVGRKEQSDDELKALKGLTEIKGSISIRIYSKYRIVEGMNDT<br>GGAAYLKSMKHLREIDITFLGECVGPEAVLETLEPPSNIKSLYIYNYSG<br>TTIPVWGRAEINWAISLSHLVDIQLSCCSNLQEMPVLSKLPHLKSLKL<br>GWLDNLEYMESSSSSDTEAATPELPTFFPSLEKLTLQHLEKLKGFGNR<br>RSSSFPPRLSELEIKKCPDLTSFPSCPSLEKLELKESNEALQIIVKITTRGK<br>EKEENNNAGVRNSQDDDKVKLRKMVIDNLGYLTGVDIRFDDREGGF<br>VNPEAVLATLEPPSNIKSLSIHRFDGKTLPVWGRAEINWAISLSHLVDI<br>QLWHCRNLQEMPVLSKLPHLKSLELYNLISLEYMESTSRSSSSDTEAA<br>TPELPTFFPSLEKLRLWYLEKLKGLGNRRPSSFPRLSELEIWECPDLTW<br>FPPCPSLKTLKLEKNNEALQIIVKITTTRGKEEKEEDKNAGVGNSQDD<br>DNVKLRKVEIDNVSYLKSLPTNCLTHLKITGIDYREGEIESDSVEEEIE<br>LEVGEAFQKCASSLRSLIIIGNHGINKVMRLSGRTGLEHFTLLDSLKFS<br>KIEDQEDEGEDNIIFWKSFPQNLRSLRIKDSDKMTSLPMGMQYLTSLQ<br>TLELSYCDELNSLPEWISSLSSLQYLRIYYCPALKSLPEAMRNLTSLQT<br>LGISDCPDLVKRCRKPNGKDYPKIQHIPKILLNTSLILNAPNLQDMD* |
| (SEQ ID NO: 6):<br>Forward primer<br>LRR domain<br>(Alpha) | ACAAGTGGATGTGTCTTAGG |
| (SEQ ID NO: 7):<br>Reverse primer<br>LRR domain | TTCGCCCTCATCTTCCTGG |
| (SEQ ID NO: 8):<br>Forward primer<br>LRR domain<br>(Beta) | TCACGTGGGTTGTGTTGT |
| (SEQ ID NO: 9):<br>Amplicon of<br>LRR domain of<br>the alpha-WOLF<br>15 allele | ACAAGTGGATGTGTCTTAGGATGTTGGACTTGTCATGGTCGGATGT<br>TAAAAATTTGCCTAATTCAATAGGTAAATTGTTGCACTTGAGGTAT<br>CTTAACCTGTCAGATAATAGAAATCTAAAGATACTTCCTGATGCA<br>ATTACAAGACTGCATAATTTGCAGACACTGCTTTTAGAAGATTGCA<br>GAAGTTTAAAGGAGTTGCCAAAAGATTTTTGCAAATTGGTCAAAC<br>TGAGGCACTTGGAATTACAGGGTTGTCATGATTTGATTGGTATGCC<br>ATTTGGAATGGATAAGCTAACTAGTCTTAGAATACTACCAAACAT<br>TGTGGTGGGTAGGAAGGAACAAAGTGATGATGAGCTGAAAGCCCT<br>AAAAGGCCTCACCGAGATAAAAGGCTCCATTTCTATCAGAATCTA<br>TTCAAAGTATAGAATAGTTGAAGGCATGAATGACACAGGAGGAGC<br>TGCTTATTTGAAGAGCATGAAACATCTCAGGGAGATTGATATTAT<br>ATTTTTGGGTGAATGTGTTGGCCCTGAAGCTGTATTGGAAACCTTA<br>GAGCCACCTTCAAATATCAAGAGCTTATATATATATAATTACAGTG<br>GTACAACAATTCCAGTATGGGAAGAGCAGAGATTAATTGGGCAA<br>TCTCCCTCTCACATCTCGTCGACATCCAGCTTAGTTGTTGTAGTAA<br>TTTGCAGGAGATGCCAGTGCTGAGTAAACTGCCTCATTTGAAATC |

TABLE 2-continued

Sequence Information

|  |  |
|---|---|
|  | GCTGAAACTTGGATGGTTGGATAACTTAGAGTACATGGAGAGTAG<br>CAGTAGCAGTGACACAGAAGCAGCAACACCAGAATTACCAACATT<br>CTTCCCTTCCCTTGAAAAACTTACTTTACAGCATCTGGAAAAGTTG<br>AAGGGTTTTGGGAACAGGAGATCGAGTAGTTTTCCCCGCCTCTCTG<br>AATTGGAAATCAAGAAATGCCCAGATCTAACGTCATTTCCTTCTTG<br>TCCAAGCCTTGAGAAGTTGGAATTGAAAGAAAGCAATGAAGCATT<br>GCAAATAATAGTAAAAATAACAACAAGAGGTAAAGAAAAAGAAG<br>AGAACAATAATGCTGGTGTTAGAAATTCACAAGATGATGACAAAG<br>TCAAATTACGGAAGATGGTGATAGACAATCTGGGTTATCTCACGG<br>GGGTTGATATTAGATTTGATGATAGAGAAGGTGGATTTGTTAACC<br>CTGAAGCTGTGTTGGCAACCCTAGAGCCACCTTCAAATATCAAGA<br>GCTTATCTATACATCGTTTTGATGGTAAAACACTTCCAGTATGGGG<br>AAGAGCAGAGATTAATTGGGCAATCTCCCTCTCACATCTTGTCGAC<br>ATCCAGCTTTGGCATTGTCGTAATTTGCAGGAGATGCCAGTGCTGA<br>GTAAACTGCCTCATTTGAAATCACTGGAACTTTATAATTTGATTAG<br>TTTAGAGTACATGGAGAGCACAAGCAGAAGCAGTAGCAGTGACA<br>CAGAAGCAGCAACACCAGAATTACCAACATTCTTCCCTTCCCTTGA<br>AAAACTTAGACTTTGGTATCTGGAAAAGTTGAAGGGTTTGGGGAA<br>CAGGAGACCGAGTAGTTTTCCCCGCCTCTCTGAATTGGAAATCTGG<br>GAATGCCCAGATCTAACGTGGTTTCCTCCTTGTCCAAGCCTTAAAA<br>CGTTGAAATTGGAAAAAAACAATGAAGCGTTGCAAATAATAGTAA<br>AAATAACAACAACAAGAGGTAAAGAAGAAAAAGAAGAAGACAA<br>GAATGCTGGTGTTGGAAATTCACAAGATGATGACAATGTCAAATT<br>ACGGAAGGTGGAAATAGACAATGTGAGTTATCTCAAATCACTGCC<br>CACAAATTGTCTTACTCACCTCAAAATAACTGGAATAGATTACAG<br>GGAGGGGGAGATTGAATCAGATTCCGTGGAGGAGGAGATTGAATT<br>GGAAGTTGGGGAGGCATTTCAGAAGTGTGCATCTTCTTTGAGAAG<br>CCTCATCATAATCGGAAATCACGGAATAAATAAAGTGATGAGACT<br>GTCTGGAAGAACAGGGTTGGAGCATTTCACTCTGTTGGACTCACTC<br>AAATTTTCAAAGATAGAAGACCAGGAAGATGAGGGCGAA |
| (SEQ ID NO: 10):<br>amino acid<br>sequence<br>encoded by<br>amplicon of LRR<br>domain of alpha-<br>WOLF 15 | KWMCLRMLDLSWSDVKNLPNSIGKLLHLRYLNLSDNRNLKILP<br>DAITRLHNLQTLLLEDCRSLKELPKDFCKLVKLRHLELQGCHD<br>LIGMPFGMDKLTSLRILPNIVVGRKEQSDDELKALKGLTEIKGSI<br>SIRIYSKYRIVEGMNDTGGAAYLKSMKHLREIDITFLGECVGPE<br>AVLETLEPPSNIKSLYIYNYSGTTIPVWGRAEINWAISLSHLVDI<br>QLSCCSNLQEMPVLSKLPHLKSLKLGWLDNLEYMESSSSSDTE<br>AATPELPTFFPSLEKLTLQHLEKLKGFGNRRSSSFPRLSELEIKK<br>CPDLTSFPSCPSLEKLELKESNEALQIIVKITTRGKEKEENNNAG<br>VRNSQDDDKVKLRKMVIDNLGYLTGVDIRFDDREGGFVNPEA<br>VLATLEPPSNIKSLSIHRFDGKTLPVWGRAEINWAISLSHLVDIQ<br>LWHCRNLQEMPVLSKLPHLKSLELYNLISLEYMESTSRSSSSDT<br>EAATPELPTFFPSLEKLRLWYLEKLKGLGNRRPSSFPRLSELEIW<br>ECPDLTWFPPCPSLKTLKLEKNNEALQIIVKITTTRGKEEKEEDK<br>NAGVGNSQDDDNVKLRKVEIDNVSYLKSLPTNCLTHLKITGID<br>YREGEIESDSVEEEIELEVGEAFQKCASSLRSLIIIGNHGINKVMR<br>LSGRTGLEHFTLLDSLKFSKIEDQEDEGE |
| (SEQ ID NO: 11):<br>Amplicon of<br>LRR domain of<br>the beta-WOLF 0<br>allele | TCACGTGGGTTGTGTTGTCGATAGAGATCCAGAAATAGTCTT<br>TTTATGTAGCAATAAGATTCGTTCGTATATTAGCGGTCGCTG<br>CATAAAGAATCCGGTGGATTCACAAATAGACAACTGGATGT<br>GCCTTAGGGTGTTGGACTTGTCAGATTCATGTGTTAAAGATT<br>TGTCTGATTCAATAGGTAAGCTGCTGCACTTAAGGTATCTTA<br>ACCTCTCTTCTAATATAAAGTTGGAGATAATCCCTGATGCAA<br>TTACAAGACTGCATAACTTGCAGACACTACTTTTAGAAGATT<br>GCAGAAGTTTAAAGGAGTTGCCAAAAGATTTTTGCAAATTG<br>GTCAAACTGAGGCACTTGGAATTACAGGGTTGTCATGATTTG<br>ATTGGTATGTCATTTGGAATGGATAAGCTAACTAGTCTTAGA<br>ATACTACCAAACATTGTGGTGGGTAGGAAGGAACAAAGTGT<br>TGATGATGAGCTGAAAGCCCTAAAAGGCCTCACCGAGATAA<br>AAGGCTCCATTGATATCACAATCTATTCAAAATATAGAAGA<br>GTTGAAGGCATGAATGGCACAGGAGGAGGAGCTGGGTATTT<br>GAAGAGCATGAAACATCTCACGGGGGTTAATATTACATTTG<br>ATGAAGGTGGATGTGTTAACCCTGAAGCTGTGTATTTGAAG<br>AGCATGAAACATCTCACGAGGGTTATTATTATATTTGATTAT<br>AAAGGTGGATGTGTTAACCCTGAAGCTGTGTTGGCAACCCT<br>AGAGCCACCTTCAAATATCAAGAGGTTAGAGATGTGGCATT<br>ACAGTGGTACAACAATTCCAGTATGGGGAAGAGCAGAGATT<br>AATTGGGCAATCTCCCTCTCACATCTTGTCGACATCACGCTT<br>GAAGATTGTTACAATTTGCAGGAGATGCCAGTGCTGAGTAA<br>ACTGCCTCATTTGAAATCACTGGAACTTACAGAGTTGGATAA<br>CTTAGAGTACATGGAGAGTAGAAGCAGCAGCAGTAGCAGTG<br>ACACAGAAGCAGCAACACCAGAATTACCAACATTCTTCCCT<br>TCCCTTGAAAAACTTACACTTTGGCGTCTGGACAAGTTGAAG<br>GGTTTTGGGAACAGGAGATCGAGTAGTTTTCCCCGCCTCTCT<br>AAATTGGAAATCTGGAAATGTCCAGATCTAACGTCATTTCCT<br>TCTTGTCCAAGCCTTGAGAGTTGGAATTGAAAGAAAACAA<br>TGAAGCGTTGCAAATAATAGTAAAAATAACAACAACAAGAG |

TABLE 2-continued

Sequence Information

```
                    GTAAAGAAGAAAAAGAAGAAGACAAGAATGCTGGTGTTGG
                    AAATTCACAAGATGATGACAATGTCAAATTATGGAAGGTGG
                    AAATAGACAATCTGGGTTATCTCAAATCACTGCCCACAAATT
                    GTCTGACTCACCTCGACCTTACAATAAGTGATTCCAAGGAGG
                    GGGAGGGTGAATGGGAAGTTGGGGATGCATTTCAGAAGTGT
                    GTATCTTCTTTGAGAAGCCTCACCATAATCGGAAATCACGGA
                    ATAAATAAAGTGAAGAGACTGTCTGGAAGAACAGGGTTGGA
                    GCATTTCACTCTGTTGGAATCACTCAAACTTTCAGATATAGA
                    AGACCAGGAAGATGAGGGCGAA
```

| | |
|---|---|
| (SEQ ID NO: 12):<br>amino acid<br>sequence<br>encoded by<br>amplicon of LRR<br>domain Beta<br>Wolf 0 (Viroflay) | HVGCVVDRDPEIVFLCSNKIRSYISGRCIKNPVDSQIDNWMCLR<br>VLDLSDSCVKDLSDSIGKLLHLRYLNLSSNIKLEIIPDAITRLHNL<br>QTLLLEDCRSLKELPKDFCKLVKLRHLELQGCHDLIGMSFGMD<br>KLTSLRILPNIVVGRKEQSVDDELKALKGLTEIKGSIDITIYSKYR<br>RVEGMNGTGGGAGYLKSMKHLTGVNITFDEGGCVNPEAVYL<br>KSMKHLTRVIIIFDYKGGCVNPEAVLATLEPPSNIKRLEMWHYS<br>GTTIPVWGRAEINWAISLSHLVDITLEDCYNLQEMPVLSKLPHL<br>KSLELTELDNLEYMESRSSSSSSDTEAATPELPTFFPSLEKLTLW<br>RLDKLKGFGNRRSSSFPRLSKLEIWKCPDLTSFPSCPSLEELELK<br>ENNEALQIIVKITTTRGKEEKEEDKNAGVGNSQDDDNVKLWK<br>VEIDNLGYLKSLPTNCLTHLDLTISDSKEGEGEWEVGDAFQKC<br>VSSLRSLTIIGNHGINKVKRLSGRTGLEHFTLLESLKLSDIEDQE<br>DEGE |

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Testing for Resistance to *Peronospora farinosa* f. sp. *spinaciae* in Spinach Plants The resistance to downy mildew infection was assayed as described by Irish et al. (2008; Phytopathol. 98: 894-900), using a differential set. Spinach plants of the invention were sown along with spinach plants from different other genotypes (see Table 3) in trays containing Scotts Redi-Earth medium, and fertilized twice a week after seedling emergence with Osmocote Peter's (13-13-13) fertilizer (Scotts). Plants were inoculated with a sporangial suspension (2.5× 10$^5$/ml) of a pathogenic race of *Peronospora farinosa* f. sp. *spinaciae* at the first true leaf stage. In this manner, 16 officially recognized pathogenic races were tested.

The inoculated plants were placed in a dew chamber at 18° C. with 100% relative humidity for a 24 h period, and then moved to a growth chamber at 18° C. with a 12 h photoperiod for 6 days. After 6 days, the plants were returned to the dew chamber for 24 h to induce sporulation, and they were scored for disease reaction.

Plants for this specific test were scored as resistant, intermediately resistant, or susceptible based on symptoms of chlorosis and signs of pathogen sporulation on the cotyledons and true leaves, as described by Irish et al. (2007; Plant Dis. 91: 1392-1396). Plants exhibiting no evidence of chlorosis and sporulation were in this specific test considered as resistant. Resistant plants were re-inoculated to assess whether plants initially scored as resistant had escaped infection, or whether they were truly resistant. Plants that showed only symptoms of chlorosis, or sporulation occurring only on the tips of the cotyledons were scored as intermediately resistant. Plants showing more than these symptoms of downy mildew infection were scored as being susceptible.

Table 1 shows the resistance of a plant carrying the alpha-WOLF 15 allele to each one of these pathogenic races. Table 3 shows the differential set of spinach downy mildew races and the resistance of various spinach varieties (hybrids) to each one of these pathogenic races. A susceptible reaction is scored as "+" (indicating a successful infection by the fungus, with sporulation occurring on the entire cotyledon), and resistance is depicted as "−" (absence of sporulation on the cotyledons). A weak resistance response is indicated as "(−)", which in practice means a slightly reduced level of infection (with only symptoms of chlorosis, or sporulation only occurring on the tips of the cotyledons in the differential seedling test).

TABLE 3

| | plants | | | | | | | | | | | |
|---|---|---|---|---|---|---|---|---|---|---|---|---|
| Races | Viroflay | Resistoflay | Califlay | Clermont | Campania | Boeing | Lion | Lazio | Whale | Polka | Pigeon | Meerkat |
| Pfs: 1 | + | − | − | − | − | − | − | − | − | − | − | − |
| Pfs: 2 | + | − | + | − | − | − | − | − | − | − | − | − |
| Pfs: 3 | + | + | − | − | − | − | − | − | − | − | − | − |
| Pfs: 4 | + | + | + | − | − | − | − | − | (−) | + | − | − |
| Pfs: 5 | + | + | − | + | − | − | − | − | − | − | − | − |
| Pfs: 6 | + | + | + | + | + | − | − | − | (−) | + | − | − |
| Pfs: 7 | + | + | + | + | − | − | − | − | (−) | + | − | − |

TABLE 3-continued

| | plants | | | | | | | | | | | |
|---|---|---|---|---|---|---|---|---|---|---|---|---|
| Races | Viroflay | Resistoflay | Califlay | Clermont | Campania | Boeing | Lion | Lazio | Whale | Polka | Pigeon | Meerkat |
| Pfs: 8 | + | + | − | + | + | + | − | − | − | − | − | − |
| Pfs: 9 | + | + | − | + | + | − | − | − | − | − | − | − |
| Pfs: 10 | + | + | + | + | + | + | + | − | + | + | − | − |
| Pfs: 11 | + | + | − | + | − | − | − | + | − | − | − | − |
| Pfs: 12 | + | + | − | + | + | + | − | + | − | − | − | − |
| Pfs: 13 | + | + | + | + | (−) | − | − | + | + | (−) | − | − |
| Pfs: 14 | + | + | − | + | + | + | − | + | (−) | − | + | − |
| Pfs: 15 | + | + | + | − | − | − | − | − | + | + | − | − |
| Pfs: 16 | + | + | − | + | − | − | − | + | − | − | + | + |

Example 2: Amplification of the LRR Domain-Encoding Region

The isolated genomic DNA of a spinach plant comprising the alpha-WOLF 15 allele, of which a representative sample of seed was deposited with the NCIMB under NCIMB accession number 42466 was used in polymerase chain reactions (PCR), using forward primer ACAAGTGGATGTGTCTTAGG (SEQ ID NO: 6) and reverse primer TTCGCCCTCATCTTCCTGG (SEQ ID NO: 7). The primer pair amplifies the LRR domain-encoding region of an alpha-WOLF gene, and has been designed for selectively amplifying part of a WOLF gene, and not of other CC-NBS-LRR protein-encoding genes.

PCR conditions for amplifying the LRR domain-encoding region of an alpha-WOLF gene using primers having (SEQ ID NO: 6) and (SEQ ID NO: 7) were as follows, using Platinum Taq enzyme (Thermo Fisher Scientific):
- 3 minutes at 95° C. (initial denaturing step)
- 40 amplification cycles, each cycle consisting of: 30 seconds denaturation at 95° C., 30 seconds annealing at 60° C., and 30 seconds extension at 72° C.
- 2 minutes at 72° C. (final extension step)

The isolated genomic DNA of a spinach plant of variety Viroflay comprising the beta-WOLF 0 allele was used in polymerase chain reactions (PCR), using forward primer TCACGTGGGTTGTGTTGT (SEQ ID NO: 8) and reverse primer TTCGCCCTCATCTTCCTGG (SEQ ID NO: 7). The primer pair amplifies the LRR domain-encoding region of a beta-WOLF gene, and has been designed for selectively amplifying part of a WOLF gene, and not of other CC-NBS-LRR protein-encoding genes.

PCR conditions for amplifying the LRR domain-encoding region of a beta-WOLF gene using primers having (SEQ ID NO: 7) and (SEQ ID NO: 8) were as follows, using Platinum Taq enzyme (Thermo Fisher Scientific):
- 3 minutes at 95° C. (initial denaturing step)
- 40 amplification cycles, each cycle consisting of: 30 seconds denaturation at 95° C., 50 seconds annealing at 58° C. and 50 seconds extension at 72° C.
- 2 minutes at 72° C. (final extension step)

The PCR products were visualized on agarose gel (not shown), and DNA was purified from the PCR reaction. Subsequently the sequence of the PCR products was determined using methods well known in the art.

The sequence of the LRR domain of the alpha WOLF 15 allele amplified by primers having (SEQ ID NO: 6) and (SEQ ID NO: 7) is provided in Table 2 under (SEQ ID NO: 9).

The sequence of the LRR domain of the beta-WOLF 0 allele amplified by primers having (SEQ ID NO: 7) and (SEQ ID NO: 8) is provided in Table 2 under (SEQ ID NO: 11).

Finally, the obtained sequences were translated into the corresponding amino acid sequence of the LRR domain having (SEQ ID NO: 10) and (SEQ ID NO: 12) for the alpha-WOLF 15 allele and the beta-WOLF 0, respectively (See also Table 2).

If PCR products were to be sequenced using SMRT sequencing (Pacific Biosciences), PCR primers and PCR conditions were different.

To the above-mentioned forward primers the following standard amplification sequence was added: GCAGTCGAACATGTAGCTGACTCAGGTCAC (SEQ ID NO: 17).

To the reverse primer, the following standard amplification sequence was added: TGGATCACTTGTGCAAGCATCACATCGTAG (SEQ ID NO: 18).

Example 3: Introducing Alpha-WOLF 15 Allele in a Plant not Carrying the Allele A spinach plant comprising the alpha-WOLF 15 allele, of which a representative sample of seed was deposited with the NCIMB under NCIMB accession number 42466 was crossed with a plant of variety Viroflay carrying the beta-WOLF 0 allele to obtain a F1 generation. Subsequently, a F1 plant was selfed to obtain a F2 population.

Plants of the F2 population were assayed as described in Example 1 for resistance to *Peronospora farinosa* f. sp. *spinaciae* pfs:15. Approximately 75% of the plants scored completely resistant in the assay.

Genomic DNA of each plant of the same F2 population was isolated and used in two different polymerase chain reactions (PCR). The first PCR reaction was done using primers for amplifying the LRR domain of an alpha-WOLF allele and the second PCR reaction was done using primers for amplifying the LRR domain of a beta-WOLF allele, both as described in Example 2.

The PCR products were visualized on agarose gel (not shown), this demonstrated that approximately 25% of the plant only contained an alpha-WOLF fragment, approximately 50% contained both an alpha- and a beta-WOLF fragment, and that the remaining approximately 25% of the plants only contained a beta-WOLF fragment. The plants containing the alpha-WOLF fragment completely correlated with the plants that scored resistant for pfs:15. The plants only comprising the beta-WOLF fragment completely correlated with the plants that scored susceptible for pfs:15.

DNA from the PCR reaction was purified, and subsequently the sequence of the PCR products was determined. The alpha-WOLF PCR products gave a sequence that corresponded to the sequence of (SEQ ID NO: 9), the genomic sequence of the LRR domain of the alpha-WOLF 15 allele. The beta-WOLF PCR products gave a sequence that corresponded to the sequence of (SEQ ID NO: 11) the genomic sequence of the LRR domain of the beta-WOLF 0 allele.

The invention is further described by the following numbered paragraphs:

1. An allele designated alpha-WOLF 15 which confers resistance to at least one *Peronospora farinosa* f. Sp. *spinacea* race when present in a spinach plant, wherein the protein encoded by said allele is a CC-NBS-LRR protein that comprises in its amino acid sequence: a) the motif "MAEIGYSVC" (SEQ ID NO: 13) at its N-terminus; and b) the motif "KWMCLR" (SEQ ID NO: 14); and wherein the LRR domain of the protein has in order of increased preference at least 92%, 93%, 94%, 95%, 96%, 97%, 98%, 99%, 100% sequence similarity to (SEQ ID NO: 10).

2. The allele of paragraph 1, wherein the allele when homozygously present in a spinach plant confers complete resistance to *Peronospora farinosa* f. Sp. *spinacea* races pfs:1, pfs:2, pfs:3, pfs:4 and pfs: 5, pfs:6, pfs:8, pfs:9, pfs:11, pfs:12, pfs:13, pfs:14, pfs:15, pfs:16 and isolates UA1014 and US1508, and confers intermediate resistance to pfs:10, and does not confer resistance to pfs:7.

3. The allele of paragraph 1 or 2, wherein the allele has a genomic nucleotide sequence which in order of increased preference has at least 80%, 81%, 82%, 83%, 84%,85%, 86%, 87%, 88%, 89%, 90%, 91%, 92%, 93%, 94%, 95%, 96%, 97%, 98%, 99%, 100% sequence similarity to (SEQ ID NO: 1).

4. The allele of paragraph 1 or 2, wherein the allele has a coding sequence which in order of increased preference has at least 80%, 81%, 82%, 83%, 84%,85%, 86%, 87%, 88%, 89%, 90%, 91%, 92%, 93%, 94%, 95%, 96%, 97%, 98%, 99%, 100% sequence similarity to (SEQ ID NO: 2).

5. The allele of paragraph 1 or 2, wherein the allele has a coding sequence which in order of increased preference has at least 80%, 81%, 82%, 83%, 84%,85%, 86%, 87%, 88%, 89%, 90%, 91%, 92%, 93%, 94%, 95%, 96%, 97%, 98%, 99%, 100% sequence similarity to (SEQ ID NO: 3).

6. The allele of paragraph 1 or 2, wherein the allele encodes a protein having an amino acid sequence which in order of increased preference has at least 92%, 93%, 94%, 95%, 96%, 97%, 98%, 99%, 100% sequence similarity to (SEQ ID NO: 4).

7. The allele of paragraph 1 or 2, wherein the allele encodes for a protein having an amino acid sequence which in order of increased preference has at least 92%, 93%, 94%, 95%, 96%, 97%, 98%, 99%, 100% sequence similarity to (SEQ ID NO: 5).

8. A method of producing a hybrid spinach seed comprising crossing a first parent spinach plant with a second parent spinach plant and harvesting the resultant hybrid spinach seed, wherein said first parent spinach plant comprises the allele of any of the paragraphs 1 to 7.

9. The method of paragraph 8, wherein the first and/or second parent is a plant of an inbred line.

10. A hybrid spinach plant grown from the seed produced by the method of paragraph 8 or paragraph 9.

11. Method for identifying or selecting a spinach plant carrying the allele of any of the paragraphs 1 to 7, comprising determining the presence of a genomic nucleotide sequence or a part thereof in the genome of a plant, wherein said sequence has in order of increased preference 80%, 81%, 82%, 83%, 84%,85%, 86%, 87%, 88%, 89%, 90%, 91%, 92%, 93%, 94%, 95%, 96%, 97%, 98%, 99%, 100% sequence similarity to (SEQ ID NO: 1).

12. Method for identifying or selecting a spinach plant carrying the allele of any of the paragraphs 1-4 and 6, comprising determining the presence of a genomic nucleotide sequence or a part thereof in the genome of a plant, wherein said sequence has in order of increased preference 80%, 81%, 82%, 83%, 84%,85%, 86%, 87%, 88%, 89%, 90%, 91%, 92%, 93%, 94%, 95%, 96%, 97%, 98%, 99%, 100% sequence similarity to (SEQ ID NO: 2).

13. Method for identifying or selecting a spinach plant carrying the allele of any of the paragraphs 1-3, 5 and 7, comprising determining the presence of a genomic nucleotide sequence or a part thereof in the genome of a plant, wherein said sequence has in order of increased preference 80%, 81%, 82%, 83%, 84%,85%, 86%, 87%, 88%, 89%, 90%, 91%, 92%, 93%, 94%, 95%, 96%, 97%, 98%, 99%, 100% sequence similarity to (SEQ ID NO: 3).

14. The method of any of the paragraphs 11 to 13, comprising determining the presence of the LRR domain as defined in paragraph 1.

15. The method of paragraph 14, wherein the LRR domain is determined by using a primer pair to amplify the LRR domain, wherein the forward primer is a nucleic acid molecule having the sequence of (SEQ ID NO: 6).

16. The method of paragraph 14, wherein the LRR domain is determined by using a primer pair to amplify the LRR domain, wherein the reverse primer is a nucleic acid molecule having the sequence of (SEQ ID NO: 7).

17. Primer pair comprising a forward primer which is a nucleic acid molecule having the sequence of (SEQ ID NO: 6) and a reverse primer which is a nucleic acid molecule having the sequence of (SEQ ID NO: 7).

18. A method for producing a spinach plant showing resistance to *Peronospora farinosa* f. sp. *spinaciae* comprising: (a) crossing a plant comprising the allele of any one of the paragraphs 1 to 9, with another plant; (b) optionally performing one or more rounds of selfing and/or crossing; (c) selecting after one or more rounds of selfing and/or crossing for a plant that comprises said allele of any of the paragraphs 1 to 7.

19. The method of paragraph 21, wherein the selection of a plant comprising the allele comprises determining the presence of the allele according the method of anyone of the paragraphs 11 to 16.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying or selecting a spinach plant carrying an allele designated alpha-WOLF 15 which confers resistance to at least one *Peronospora farinosa* f. sp. *spinaciae* race when present in a spinach plant, wherein the protein encoded by said allele is a CC-NBS-LRR protein that comprises in its amino acid sequence: a) the motif SEQ ID NO: 13 at its N-terminus and b) the motif SEQ ID NO: 14; and wherein the LRR domain of the protein has at least 98% sequence identity to SEQ ID NO: 10, comprising determining the presence of a nucleotide sequence or a part thereof in a plant, wherein said sequence has at least 95% sequence identity to SEQ ID NO: 1.

2. A method for identifying or selecting a spinach plant carrying an allele designated alpha-WOLF 15 which confers resistance to at least one *Peronospora farinosa* f. sp. *spinaciae* race when present in a spinach plant, wherein the protein encoded by said allele is a CC-NBS-LRR protein that comprises in its amino acid sequence: a) the motif SEQ ID NO: 13 at its N-terminus and b) the motif SEQ ID NO: 14; and wherein the LRR domain of the protein has at least 98% sequence identity to SEQ ID NO: 10, comprising determining the presence of a nucleotide sequence or a part thereof in a plant, wherein said sequence has at least 99% sequence identity to SEQ ID NO: 2.

3. A method for identifying or selecting a spinach plant carrying an allele designated alpha-WOLF 15 which confers resistance to at least one *Peronospora farinosa* f. sp. *spinaciae* race when present in a spinach plant, wherein the protein encoded by said allele is a CC-NBS-LRR protein that comprises in its amino acid sequence: a) the motif SEQ ID NO: 13 at its N-terminus and b) the motif SEQ ID NO: 14; and wherein the LRR domain of the protein has at least 98% sequence identity to SEQ ID NO: 10, comprising determining the presence of a nucleotide sequence or a part thereof in a plant, wherein said sequence has at least 99% sequence identity to SEQ ID NO: 3.

* * * * *

UNITED STATES PATENT AND TRADEMARK OFFICE
CERTIFICATE OF CORRECTION

| | |
|---|---|
| PATENT NO. | : 11,203,766 B2 |
| APPLICATION NO. | : 16/361491 |
| DATED | : December 21, 2021 |
| INVENTOR(S) | : Vincent Laurens Adrianus Kock et al. |

It is certified that error appears in the above-identified patent and that said Letters Patent is hereby corrected as shown below:

On the Title Page

Item (71), should read:
(71) Applicant: RIJK ZWAAN ZAADTEELT EN ZAADHANDEL B.V., De Lier (NL)

Signed and Sealed this
Twelfth Day of July, 2022

Katherine Kelly Vidal
*Director of the United States Patent and Trademark Office*